US009670284B2

(12) United States Patent
Qi et al.

(10) Patent No.: US 9,670,284 B2
(45) Date of Patent: Jun. 6, 2017

(54) THERAPEUTIC USES FOR VEGFR1 ANTIBODIES

(71) Applicant: ELI LILLY AND COMPANY, Indianapolis, IN (US)

(72) Inventors: Zhonghua Qi, Carmel, IN (US); Matthew Douglas Breyer, Indianapolis, IN (US); Ling Liu, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/203,675

(22) Filed: Mar. 11, 2014

(65) Prior Publication Data

US 2014/0271675 A1 Sep. 18, 2014

Related U.S. Application Data

(60) Provisional application No. 61/788,870, filed on Mar. 15, 2013.

(51) Int. Cl.
*A61K 39/395* (2006.01)
*C07K 16/28* (2006.01)
*A61K 39/00* (2006.01)

(52) U.S. Cl.
CPC .... *C07K 16/2863* (2013.01); *A61K 2039/505* (2013.01); *C07K 2317/33* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| 7,972,596 | B2 | 7/2011 | Wu et al. | |
|---|---|---|---|---|
| 8,143,025 | B2 | 3/2012 | Wu et al. | |
| 2011/0269186 | A1* | 11/2011 | Wu .................. | A61K 39/39541 435/69.6 |
| 2011/0286983 | A1* | 11/2011 | Pearlman ............. | C07K 14/505 424/93.21 |

FOREIGN PATENT DOCUMENTS

WO 2006055809 A2 5/2006

OTHER PUBLICATIONS

Eremina V et al., "VEGF Inhibition and Renal Thrombotic Microangiopathy", The New England Journal of Medicine, pp. 1129-1136, Mar. 2008.
Veron D et al., "Overexpression of VEGF-A in podocytes of adult mice causes glomerular disease", Kidney International, No. 77, pp. 989-999, 2010.

Hakroush S et al., "Effects of Increased Renal Tubular Vascular Endothelial Growth Factor (VEGF) on Fibrosis, Cyst Formation, and Glomerular Disease", The American Journal of Pathology, vol. 175, No. 5, pp. 1883-1895, Nov. 2009.
Cha D et al, "Role of Vascular Endothelial Growth Factor in Diabetic Nephrophathy", Kidney International, vol. 58, Suppl. 77, pp. S104-S112, 2000.
Hovind P et al, "Elevated Vascular Endothelial Growth Factor in Type 1 Diabetic patients with Diabetic Nephropathy", Kidney International, No. 57, Suppl. 75, pp. S56-S61, 2000.
de Vriese et al, "Antibodies against Vascular Endothelial Growth Factor Improve Early Renal Dysfunction in Experimental Diabetes", Journal Americal Society Nephrology, No. 12, pp. 993-1000, 2001.
Flyvbjerg A et al, "Amerlioration of Long-Term Renal Changes in Obese Type 2 Diabetic Mice by a Neutralizing Vascular Endothelial Growth Factor Antibody", Diabetes, No. 51, pp. 3090-3094.
Doi K et al, "Role of Vascular Endothelial Growth Factor in Kidney Disease", Current Vascular Pharmacology, No. 8, pp. 122-128, 2010.
Toblli J et al, "Understanding the Mechanisms of Proteinuria: Therapeutic Implications", International Journal Nephrology, Article ID 546039, 2012.
Sato et al, "Selective Stimulation of VEGFR2 Accelerates Progressive Renal Disease", The American Journal of Pathology, vol. 179, No. 1, pp. 155-166, Jul. 2011.
Ku C et al, "Inducible Overexpression of sFlt-1 in Podocytes Ameliorates Glomerulopathy in Diabetic Mice", Diabetes, No. 57, pp. 2824-2833, 2008.
DiMarco S et al, "The Soluble VEGF Receptor sFlt1 Contributes to Endothelial Dysfunction in CKD", Journal of the American Society of Nephrology, vol. 20, No. 10, pp. 2235-2245, Oct. 1, 2009.
Kim H W et al, "Long-term blockade of vascular endothelial growth factor receptor-2 aggravates the diabetic renal dysfunction associated with inactivation of the Akt/eNOS—NO axis", Nephrology Dialysis Transplantion, vol. 26, pp. 1173-1188, 2011.
Chade A et al, "VEGF: Potential therapy for renal regeneration", F1000 Reports Medicine, Jan. 2012.
Xu L et al, "Diabetic angiopathy and angiogenic defects", Fibrogenesis & Tissue Repair, No. 5:13, 2012.
Huang H et al, Blockade of VEGFR1 and 2 Suppresses Pathological Angiogenesis and Vascular Leakage in the Eye, PLoS One, No. 6, e21411, Jun. 2011.
Müller-Deile, J., et al., "Renal Involvement in Preeclampsia: Similarities to VEGF Ablation Therapy," Journal of Pregnancy, vol. 19, No. 6, pp. 729-734, 2011.
Sung, S.H., et al., "Blockade of Vascular Endothelial Growth Factor Signaling Ameliorates Diabetic Albuminuria in Mice," Journal of the American Society of Nephrology, vol. 17, No. 11, pp. 3093-3104, 2006.
Patent Cooperation Treaty International Search Report and Written Opinion of the International Searching Authority pertaining to International Application No. PCT/US2014/022925; Date of Mailing, Jul. 4, 2014.
Fine, L., et al., Chronic Hypoxia as a Mechanism of Progression of Chronic Kidney Diseases: From Hypothesis to Novel Therapeutics, Kidney International, 2008, 74, pp. 867-872.
Fioretto, P., et al., Reversal of Lesions of Diabetic Nephropathy After Pancreas Transplatation, New England Journal of Medicine, 1998, vol. 339., No. 2, pp. 69-75.

(Continued)

*Primary Examiner* — Michael Pak
(74) *Attorney, Agent, or Firm* — Jennifer K. Gregory; Matthew T. Lord

(57) ABSTRACT

The present invention relates to methods of using VEGFR1 antibodies for the treatment of chronic kidney disease.

8 Claims, No Drawings

(56) References Cited

OTHER PUBLICATIONS

Ma, L., et al., Model of Robust Induction Gloemeruloscleosis in Mice: Importance of Genetic Background, Kidney International, 2003, vol. 64, pp. 350-355.
Parving, H., Initiation and Progression of Diabetic Nephropathy, New England Journal of Medicine, Nov. 28, 1996, vol. 335, No. 22, pp. 1682-1683.
Steffes, M., et al., Mesangial Expansion as a Central Mechanism for Loss of Kidney Function in Diabetic Patients, Sep. 1989, Diabetes, vol. 38, pp. 1077-1081.
Turner, J., et al. Treatment of Chronic Kidney Disease, Kidney International, 2012, 81, pp. 351-362.
Letter Accompanying Demand for International Preliminary Examination Pursuant to Article 31 of the PCT, submitted by Matthew T. Lord in PCT/US2014/022925, dated Jan. 15, 2015.
Patent Cooperation Treaty International Preliminary Report on Patentability pertaining to International Application No. PCT/US2014/022925. Date of Mailing: Apr. 2, 2015.
Middleton, "The unrecognized prevalence of chronic kidney disease in diabetes", Nephrology Dialysis Transplantation, 2006, pp. 88-92, vol. 21.
Sugimoto, "Neutralization of Circulating Vascular Endothelial Growth Factor (VEGF) by Anti-VEGF Antibodies and Soluble VEGF Receptor 1 (sFlt-1) Induces Proteinuria", The Journal of Biological Chemistry, 2003, pp. 12605-12608, vol. 278, No. 15.
Khamaisi et al., The emerging role of VEGF in diabetic kidney disease, Nephrol Dial Transplant (2003), 1427-1430; vol. 18.

\* cited by examiner

SEQUENCE LISTING

<160> NUMBER OF SEQ ID NOS: 19

<210> SEQ ID NO 1
<211> LENGTH: 1338
<212> TYPE: PRT
<213> ORGANISM: Homo sapiens

<400> SEQUENCE: 1

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
                20                  25                  30

Glu Leu Ser Leu Lys Gly Thr Gln His Ile Met Gln Ala Gly Gln Thr
            35                  40                  45

Leu His Leu Gln Cys Arg Gly Glu Ala Ala His Lys Trp Ser Leu Pro
        50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285

Ala Asn Ile Phe Tyr Ser Val Leu Thr Ile Asp Lys Met Gln Asn Lys
290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365
```

```
Trp Leu Lys Asp Gly Leu Pro Ala Thr Glu Lys Ser Ala Arg Tyr Leu
370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
                420                 425                 430

Lys Ala Val Ser Ser Phe Pro Asp Pro Ala Leu Tyr Pro Leu Gly Ser
                435                 440                 445

Arg Gln Ile Leu Thr Cys Thr Ala Tyr Gly Ile Pro Gln Pro Thr Ile
450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
                500                 505                 510

Glu Gly Lys Asn Lys Met Ala Ser Thr Leu Val Val Ala Asp Ser Arg
                515                 520                 525

Ile Ser Gly Ile Tyr Ile Cys Ile Ala Ser Asn Lys Val Gly Thr Val
                530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
                580                 585                 590

Arg Thr Val Asn Asn Arg Thr Met His Tyr Ser Ile Ser Lys Gln Lys
                595                 600                 605

Met Ala Ile Thr Lys Glu His Ser Ile Thr Leu Asn Leu Thr Ile Met
610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Asp Gln Glu Ala Pro Tyr Leu Leu Arg Asn Leu Ser Asp His Thr Val
                660                 665                 670

Ala Ile Ser Ser Ser Thr Thr Leu Asp Cys His Ala Asn Gly Val Pro
                675                 680                 685

Glu Pro Gln Ile Thr Trp Phe Lys Asn Asn His Lys Ile Gln Gln Glu
                690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
                725                 730                 735

Lys Gly Ser Val Glu Ser Ser Ala Tyr Leu Thr Val Gln Gly Thr Ser
                740                 745                 750

Asp Lys Ser Asn Leu Glu Leu Ile Thr Leu Thr Cys Thr Cys Val Ala
                755                 760                 765

Ala Thr Leu Phe Trp Leu Leu Leu Thr Leu Phe Ile Arg Lys Met Lys
770                 775                 780

Arg Ser Ser Ser Glu Ile Lys Thr Asp Tyr Leu Ser Ile Ile Met Asp
```

-continued

```
                785                 790                 795                 800
Pro Asp Glu Val Pro Leu Asp Glu Gln Cys Glu Arg Leu Pro Tyr Asp
                    805                 810                 815

Ala Ser Lys Trp Glu Phe Ala Arg Glu Arg Leu Lys Leu Gly Lys Ser
                    820                 825                 830

Leu Gly Arg Gly Ala Phe Gly Lys Val Val Gln Ala Ser Ala Phe Gly
                    835                 840                 845

Ile Lys Lys Ser Pro Thr Cys Arg Thr Val Ala Val Lys Met Leu Lys
                    850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
                    885                 890                 895

Ala Cys Thr Lys Gln Gly Gly Pro Leu Met Val Ile Val Glu Tyr Cys
                    900                 905                 910

Lys Tyr Gly Asn Leu Ser Asn Tyr Leu Lys Ser Lys Arg Asp Leu Phe
                    915                 920                 925

Phe Leu Asn Lys Asp Ala Ala Leu His Met Glu Pro Lys Lys Glu Lys
                    930                 935                 940

Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
                    965                 970                 975

Leu Ser Asp Val Glu Glu Glu Asp Ser Asp Gly Phe Tyr Lys Glu
                    980                 985                 990

Pro Ile Thr Met Glu Asp Leu Ile Ser Tyr Ser Phe Gln Val Ala Arg
                    995                 1000                1005

Gly Met Glu Phe Leu Ser Ser Arg Lys Cys Ile His Arg Asp Leu
        1010                1015                1020

Ala Ala Arg Asn Ile Leu Leu Ser Glu Asn Asn Val Val Lys Ile
        1025                1030                1035

Cys Asp Phe Gly Leu Ala Arg Asp Ile Tyr Lys Asn Pro Asp Tyr
        1040                1045                1050

Val Arg Lys Gly Asp Thr Arg Leu Pro Leu Lys Trp Met Ala Pro
        1055                1060                1065

Glu Ser Ile Phe Asp Lys Ile Tyr Ser Thr Lys Ser Asp Val Trp
        1070                1075                1080

Ser Tyr Gly Val Leu Leu Trp Glu Ile Phe Ser Leu Gly Gly Ser
        1085                1090                1095

Pro Tyr Pro Gly Val Gln Met Asp Glu Asp Phe Cys Ser Arg Leu
        1100                1105                1110

Arg Glu Gly Met Arg Met Arg Ala Pro Glu Tyr Ser Thr Pro Glu
        1115                1120                1125

Ile Tyr Gln Ile Met Leu Asp Cys Trp His Arg Asp Pro Lys Glu
        1130                1135                1140

Arg Pro Arg Phe Ala Glu Leu Val Glu Lys Leu Gly Asp Leu Leu
        1145                1150                1155

Gln Ala Asn Val Gln Gln Asp Gly Lys Asp Tyr Ile Pro Ile Asn
        1160                1165                1170

Ala Ile Leu Thr Gly Asn Ser Gly Phe Thr Tyr Ser Thr Pro Ala
        1175                1180                1185

Phe Ser Glu Asp Phe Phe Lys Glu Ser Ile Ser Ala Pro Lys Phe
        1190                1195                1200
```

```
Asn Ser Gly Ser Ser Asp Asp Val Arg Tyr Val Asn Ala Phe Lys
    1205                1210                1215

Phe Met Ser Leu Glu Arg Ile Lys Thr Phe Glu Glu Leu Leu Pro
    1220                1225                1230

Asn Ala Thr Ser Met Phe Asp Tyr Gln Gly Asp Ser Ser Thr
    1235                1240                1245

Leu Leu Ala Ser Pro Met Leu Lys Arg Phe Thr Trp Thr Asp Ser
    1250                1255                1260

Lys Pro Lys Ala Ser Leu Lys Ile Asp Leu Arg Val Thr Ser Lys
    1265                1270                1275

Ser Lys Glu Ser Gly Leu Ser Asp Val Ser Arg Pro Ser Phe Cys
    1280                1285                1290

His Ser Ser Cys Gly His Val Ser Glu Gly Lys Arg Arg Phe Thr
    1295                1300                1305

Tyr Asp His Ala Glu Leu Glu Arg Lys Ile Ala Cys Cys Ser Pro
    1310                1315                1320

Pro Pro Asp Tyr Asn Ser Val Val Leu Tyr Ser Thr Pro Pro Ile
    1325                1330                1335

<210> SEQ ID NO 2
<211> LENGTH: 10
<212> TYPE: PRT
<213> ORGANISM: Artificial Sequence
<220> FEATURE:
<223> OTHER INFORMATION: Synthetic construct

<400> SEQUENCE: 2

Gly Phe Ala Phe Ser Ser Tyr Gly Met His
1               5                   10

<210> SEQ ID NO 3
<211> LENGTH: 17
<212> TYPE: PRT
<213> ORGANISM: Artificial Sequence
<220> FEATURE:
<223> OTHER INFORMATION: Synthetic construct

<400> SEQUENCE: 3

Val Ile Trp Tyr Asp Gly Ser Asn Lys Tyr Tyr Ala Asp Ser Val Arg
1               5                   10                  15

Gly

<210> SEQ ID NO 4
<211> LENGTH: 17
<212> TYPE: PRT
<213> ORGANISM: Artificial Sequence
<220> FEATURE:
<223> OTHER INFORMATION: Synthetic construct

<400> SEQUENCE: 4

Asp His Tyr Gly Ser Gly Val His His Tyr Phe Tyr Tyr Gly Leu Asp
1               5                   10                  15

Val

<210> SEQ ID NO 5
<211> LENGTH: 126
<212> TYPE: PRT
<213> ORGANISM: Artificial Sequence
<220> FEATURE:
<223> OTHER INFORMATION: Synthetic construct
```

```
<400> SEQUENCE: 5

Gln Ala Gln Val Val Glu Ser Gly Gly Gly Val Val Gln Ser Gly Arg
1               5                   10                  15

Ser Leu Arg Leu Ser Cys Ala Ala Ser Gly Phe Ala Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Arg Gly Arg Phe Thr Ile Ser Arg Asp Asn Ser Glu Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp His Tyr Gly Ser Gly Val His His Tyr Phe Tyr Tyr Gly
            100                 105                 110

Leu Asp Val Trp Gly Gln Gly Thr Thr Val Thr Val Ser Ser
        115                 120                 125

<210> SEQ ID NO 6
<211> LENGTH: 456
<212> TYPE: PRT
<213> ORGANISM: Artificial Sequence
<220> FEATURE:
<223> OTHER INFORMATION: Synthetic construct

<400> SEQUENCE: 6

Gln Ala Gln Val Val Glu Ser Gly Gly Gly Val Val Gln Ser Gly Arg
1               5                   10                  15

Ser Leu Arg Leu Ser Cys Ala Ala Ser Gly Phe Ala Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Arg Gly Arg Phe Thr Ile Ser Arg Asp Asn Ser Glu Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp His Tyr Gly Ser Gly Val His His Tyr Phe Tyr Tyr Gly
            100                 105                 110

Leu Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
```

```
                225                 230                 235                 240
Pro Glu Leu Leu Gly Gly Pro Ser Val Phe Leu Phe Pro Pro Lys Pro
                    245                 250                 255

Lys Asp Thr Leu Met Ile Ser Arg Thr Pro Glu Val Thr Cys Val Val
                260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
        290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Glu Glu Met Thr
            355                 360                 365

Lys Asn Gln Val Ser Leu Thr Cys Leu Val Lys Gly Phe Tyr Pro Ser
        370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
            435                 440                 445

Ser Leu Ser Leu Ser Pro Gly Lys
        450                 455

<210> SEQ ID NO 7
<211> LENGTH: 452
<212> TYPE: PRT
<213> ORGANISM: Artificial Sequence
<220> FEATURE:
<223> OTHER INFORMATION: Synthetic construct

<400> SEQUENCE: 7

Gln Ala Gln Val Val Glu Ser Gly Gly Gly Val Val Gln Ser Gly Arg
1               5                   10                  15

Ser Leu Arg Leu Ser Cys Ala Ala Ser Gly Phe Ala Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Arg Gly Arg Phe Thr Ile Ser Arg Asp Asn Ser Glu Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp His Tyr Gly Ser Gly Val His His Tyr Phe Tyr Tyr Gly
            100                 105                 110

Leu Asp Val Trp Gly Gln Gly Thr Thr Val Thr Val Ser Ser Ala Ser
        115                 120                 125

Thr Lys Gly Pro Ser Val Phe Pro Leu Ala Pro Cys Ser Arg Ser Thr
```

```
                130                 135                 140
Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
                195                 200                 205

Cys Asn Val Asp His Lys Pro Ser Asn Thr Lys Val Asp Lys Arg Val
            210                 215                 220

Glu Ser Lys Tyr Gly Pro Pro Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
            275                 280                 285

Glu Val His Asn Ala Lys Thr Lys Pro Arg Glu Glu Gln Phe Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
                355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
            435                 440                 445

Leu Ser Leu Gly
        450

<210> SEQ ID NO 8
<211> LENGTH: 12
<212> TYPE: PRT
<213> ORGANISM: Artificial Sequence
<220> FEATURE:
<223> OTHER INFORMATION: Synthetic construct

<400> SEQUENCE: 8

Arg Ala Ser Gln Ser Val Ser Ser Ser Tyr Leu Ala
1               5                   10

<210> SEQ ID NO 9
<211> LENGTH: 7
<212> TYPE: PRT
```

```
<213> ORGANISM: Artificial Sequence
<220> FEATURE:
<223> OTHER INFORMATION: Synthetic construct

<400> SEQUENCE: 9

Gly Ala Ser Ser Arg Ala Thr
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic construct

<400> SEQUENCE: 10

Gln Gln Tyr Gly Ser Ser Pro Leu Thr
1               5

<210> SEQ ID NO 11
<211> LENGTH: 108
<212> TYPE: PRT
<213> ORGANISM: Artificial Sequence
<220> FEATURE:
<223> OTHER INFORMATION: Synthetic construct

<400> SEQUENCE: 11

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105

<210> SEQ ID NO 12
<211> LENGTH: 215
<212> TYPE: PRT
<213> ORGANISM: Artificial Sequence
<220> FEATURE:
<223> OTHER INFORMATION: Synthetic construct

<400> SEQUENCE: 12

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
```

```
                85                  90                  95
Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 13
<211> LENGTH: 1368
<212> TYPE: DNA
<213> ORGANISM: Artificial Sequence
<220> FEATURE:
<223> OTHER INFORMATION: Synthetic construct

<400> SEQUENCE: 13
caggcgcagg tggtggagtc tgggggaggc gtggtccagt ctggggaggtc cctgagactc    60 tcctgtgcag cgtctggatt cgccttcagt agctacggca tgcactgggt ccgccaggct   120
ccaggcaagg ggctggagtg ggtggcagtt atatggtatg atggaagtaa taaatactat   180
gcagactccg tgaggggccg attcaccatc tccagagaca attccgagaa cacgctgtat   240
ctgcaaatga acagcctgag agccgaggac acggctgtat attactgtgc gagagatcac   300
tatggttcgg gggtgcacca ctatttctac tacggtctgg acgtctgggg ccaagggacc   360
acggtcaccg tctcctcagc tagcaccaag ggcccatcgg tcttccccct ggcaccctcc   420
tccaagagca cctctggggg cacagcggcc ctgggctgcc tggtcaagga ctacttcccc   480
gaaccggtga cggtgtcgtg gaactcaggc gccctgacca gcggcgtgca caccttcccg   540
gctgtcctac agtcctcagg actctactcc ctcagcagcg tggtgaccgt gccctccagc   600
agcttgggca cccagaccta catctgcaac gtgaatcaca agcccagcaa caccaaggtg   660
gacaagagag ttgagcccaa atcttgtgac aaaactcaca catgcccacc gtgcccagca   720
cctgaactcc tggggggacc gtcagtcttc ctcttccccc caaaacccaa ggacaccctc   780
atgatctccc ggacccctga ggtcacatgc gtggtggtgg acgtgagcca cgaagaccct   840
gaggtcaagt tcaactggta cgtggacggc gtggaggtgc ataatgccaa gacaaagccg   900
cgggaggagc agtacaacag cacgtaccgt gtggtcagcg tcctcaccgt cctgcaccag   960
gactggctga atggcaagga gtacaagtgc aaggtctcca acaaagccct cccagccccc  1020
atcgagaaaa ccatctccaa agccaaaggg cagccccgag aaccacaggt gtacaccctg  1080
cccccatccc gggaggagat gaccaagaac caggtcagcc tgacctgcct ggtcaaaggc  1140
ttctatccca gcgacatcgc cgtggagtgg gagagcaatg ggcagccgga gaacaactac  1200
aagaccacgc ctcccgtgct ggactccgac ggctccttct tcctctatag caagctcacc  1260
gtggacaaga gcaggtggca gcaggggaac gtcttctcat gctccgtgat gcatgaggct  1320
```

```
ctgcacaacc actacacgca gaagagcctc tccctgtccc cgggtaaa        1368
```

<210> SEQ ID NO 14
<211> LENGTH: 1356
<212> TYPE: DNA
<213> ORGANISM: Artificial Sequence
<220> FEATURE:
<223> OTHER INFORMATION: Synthetic construct

<400> SEQUENCE: 14

```
caggcgcagg tggtggagtc tgggggaggc gtggtccagt ctggaggtc cctgagactc     60
tcctgtgcag cgtctggatt cgccttcagt agctacggca tgcactgggt ccgccaggct    120
ccaggcaagg ggctggagtg ggtggcagtt atatggtatg atggaagtaa taaatactat    180
gcagactccg tgaggggccg attcaccatc tccagagaca attccgagaa cacgctgtat    240
ctgcaaatga acagcctgag agccgaggac acggctgtat attactgtgc gagagatcac    300
tatggttcgg gggtgcacca ctatttctac tacggtctgg acgtctgggg ccaagggacc    360
acggtcaccg tctcctcagc ctccaccaag ggcccatcgg tcttccccct agcgccctgc    420
tccaggagca cctccgagag cacagccgcc ctgggctgcc tggtcaagga ctacttcccc    480
gaaccggtga cggtgtcgtg gaactcaggc gccctgacca gcggcgtgca caccttcccg    540
gctgtcctac agtcctcagg actctactcc ctcagcagcg tggtgaccgt gccctccagc    600
agcttgggca cgaagaccta cacctgcaac gtagatcaca agcccagcaa caccaaggtg    660
gacaagagag ttgagtccaa atatggtccc ccatgcccac cctgcccagc acctgaggcc    720
gccgggggac catcagtctt cctgttcccc ccaaaaccca aggacactct catgatctcc    780
cggacccctg aggtcacgtg cgtggtggtg gacgtgagcc aggaagaccc cgaggtccag    840
ttcaactggt acgtggatgg cgtggaggtg cataatgcca agacaaagcc gcgggaggag    900
cagttcaaca gcacgtaccg tgtggtcagc gtcctcaccg tcctgcacca ggactggctg    960
aacggcaagg agtacaagtg caaggtctcc aacaaaggcc tcccgtcctc catcgagaaa   1020
accatctcca aagccaaagg gcagccccga gagccacagg tgtacaccct gcccccatcc   1080
caggaggaga tgaccaagaa ccaggtcagc ctgacctgcc tggtcaaagg cttctacccc   1140
agcgacatcg ccgtggagtg ggaaagcaat gggcagccgg agaacaacta caagaccacg   1200
cctcccgtgc tggactccga cggctccttc ttcctctaca gcaggctaac cgtggacaag   1260
agcaggtggc aggagggaa tgtcttctca tgctccgtga tgcatgaggc tctgcacaac   1320
cactacacac agaagagcct ctccctgtct ctgggt                             1356
```

<210> SEQ ID NO 15
<211> LENGTH: 648
<212> TYPE: DNA
<213> ORGANISM: Artificial Sequence
<220> FEATURE:
<223> OTHER INFORMATION: Synthetic construct

<400> SEQUENCE: 15

```
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcaccgct cactttcggc    300
```

```
ggagggacca aggtggagat caaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgttag                648
```

<210> SEQ ID NO 16
<211> LENGTH: 441
<212> TYPE: PRT
<213> ORGANISM: Artificial Sequence
<220> FEATURE:
<223> OTHER INFORMATION: Synthetic construct

<400> SEQUENCE: 16

```
Gln Val Gln Leu Lys Glu Ser Gly Pro Gly Leu Val Arg Pro Ser Glu
1               5                   10                  15

Thr Leu Ser Leu Thr Cys Thr Val Ser Gly Phe Ser Leu Ser Asp Tyr
            20                  25                  30

Ser Leu Ser Trp Val Arg Arg Pro Ser Gly Lys Gly Pro Glu Trp Leu
        35                  40                  45

Gly Arg Leu Trp Phe Asp Gly Asp Thr Thr Tyr Asn Ser Ala Phe Lys
    50                  55                  60

Ser Arg Leu Thr Ile Ser Arg Asp Thr Ser Lys Asp Gln Val Phe Leu
65                  70                  75                  80

Lys Met Asn Ser Leu Gln Thr Asp Asp Thr Gly Thr Tyr Tyr Cys Thr
                85                  90                  95

Arg Asp Asp Arg Asp Phe Asp Tyr Trp Gly Gln Gly Val Met Val Thr
            100                 105                 110

Val Ser Ser Ala Glu Thr Thr Ala Pro Ser Val Tyr Pro Leu Ala Pro
        115                 120                 125

Gly Thr Ala Leu Lys Ser Asn Ser Met Val Thr Leu Gly Cys Leu Val
    130                 135                 140

Lys Gly Tyr Phe Pro Glu Pro Val Thr Val Thr Trp Asn Ser Gly Ala
145                 150                 155                 160

Leu Ser Ser Gly Val His Thr Phe Pro Ala Val Leu Gln Ser Gly Leu
                165                 170                 175

Tyr Thr Leu Thr Ser Ser Val Thr Val Pro Ser Ser Thr Trp Pro Ser
            180                 185                 190

Gln Thr Val Thr Cys Asn Val Ala His Pro Ala Ser Ser Thr Lys Val
        195                 200                 205

Asp Lys Lys Ile Val Pro Arg Asn Cys Gly Gly Asp Cys Lys Pro Cys
    210                 215                 220

Ile Cys Thr Gly Ser Glu Val Ser Ser Val Phe Ile Phe Pro Pro Lys
225                 230                 235                 240

Pro Lys Asp Val Leu Thr Ile Thr Leu Thr Pro Lys Val Thr Cys Val
                245                 250                 255

Val Val Asp Ile Ser Gln Asp Asp Pro Glu Val His Phe Ser Trp Phe
            260                 265                 270

Val Asp Asp Val Glu Val His Thr Ala Gln Thr Arg Pro Pro Glu Glu
        275                 280                 285

Gln Phe Asn Ser Thr Phe Arg Ser Val Ser Glu Leu Pro Ile Leu His
    290                 295                 300
```

Gln Asp Trp Leu Asn Gly Arg Thr Phe Arg Cys Lys Val Thr Ser Ala
305                 310                 315                 320

Ala Phe Pro Ser Pro Ile Glu Lys Thr Ile Ser Lys Pro Glu Gly Arg
            325                 330                 335

Thr Gln Val Pro His Val Tyr Thr Met Ser Pro Thr Lys Glu Glu Met
            340                 345                 350

Thr Gln Asn Glu Val Ser Ile Thr Cys Met Val Lys Gly Phe Tyr Pro
            355                 360                 365

Pro Asp Ile Tyr Val Glu Trp Gln Met Asn Gly Gln Pro Gln Glu Asn
    370                 375                 380

Tyr Lys Asn Thr Pro Pro Thr Met Asp Thr Asp Gly Ser Tyr Phe Leu
385                 390                 395                 400

Tyr Ser Lys Leu Asn Val Lys Lys Glu Lys Trp Gln Gln Gly Asn Thr
                405                 410                 415

Phe Thr Cys Ser Val Leu His Glu Gly Leu His Asn His His Thr Glu
            420                 425                 430

Lys Ser Leu Ser His Ser Pro Gly Lys
            435                 440

<210> SEQ ID NO 17
<211> LENGTH: 219
<212> TYPE: PRT
<213> ORGANISM: Artificial Sequence
<220> FEATURE:
<223> OTHER INFORMATION: Synthetic construct

<400> SEQUENCE: 17

Asp Ile Val Met Thr Gln Thr Pro Val Ser Met Ser Val Ser Leu Gly
1               5                   10                  15

Gly Gln Val Ser Ile Ser Cys Arg Ser Ser Gln Ser Leu Val Asn Asn
            20                  25                  30

Asn Gly Asn Thr Tyr Leu Ser Trp Tyr Ile Gln Lys Pro Ser Gln Ser
        35                  40                  45

Pro Gln Leu Leu Ile Tyr Lys Val Ser Asn Arg Val Ser Gly Ile Ser
    50                  55                  60

Asp Arg Phe Ser Gly Ser Gly Ser Gly Thr Asp Phe Thr Leu Lys Ile
65                  70                  75                  80

Asn Lys Ile Glu Pro Asp Asp Leu Gly Val Tyr Tyr Cys Gly Gln Asn
                85                  90                  95

Thr Gln Tyr Pro Leu Thr Phe Gly Ser Gly Thr Lys Leu Glu Ile Lys
            100                 105                 110

Arg Ala Asp Ala Ala Pro Thr Val Ser Ile Phe Pro Pro Ser Thr Glu
        115                 120                 125

Gln Leu Ala Thr Gly Gly Ala Ser Val Val Cys Leu Met Asn Asn Phe
    130                 135                 140

Tyr Pro Arg Asp Ile Ser Val Lys Trp Lys Ile Asp Gly Thr Glu Arg
145                 150                 155                 160

Arg Asp Gly Val Leu Asp Ser Val Thr Asp Gln Asp Ser Lys Asp Ser
                165                 170                 175

Thr Tyr Ser Met Ser Ser Thr Leu Ser Leu Thr Lys Ala Asp Tyr Glu
            180                 185                 190

Ser His Asn Leu Tyr Thr Cys Glu Val Val His Lys Thr Ser Ser Ser
        195                 200                 205

Pro Val Val Lys Ser Phe Asn Arg Asn Glu Cys
    210                 215

```
<210> SEQ ID NO 18
<211> LENGTH: 438
<212> TYPE: PRT
<213> ORGANISM: Artificial Sequence
<220> FEATURE:
<223> OTHER INFORMATION: Synthetic construct

<400> SEQUENCE: 18

Gln Val Gln Leu Lys Glu Ser Gly Pro Gly Leu Val Arg Pro Ser Glu
1               5                   10                  15

Thr Leu Ser Leu Thr Cys Thr Val Ser Gly Phe Ser Leu Ser Asp Tyr
            20                  25                  30

Ser Leu Ser Trp Val Arg Pro Ser Gly Lys Gly Pro Glu Trp Leu
        35                  40                  45

Gly Arg Leu Trp Phe Asp Gly Asp Thr Thr Tyr Asn Ser Ala Phe Lys
50                  55                  60

Ser Arg Leu Thr Ile Ser Arg Asp Thr Ser Lys Asp Gln Val Phe Leu
65                  70                  75                  80

Lys Met Asn Ser Leu Gln Thr Asp Asp Thr Gly Thr Tyr Tyr Cys Thr
                85                  90                  95

Arg Asp Asp Arg Asp Phe Asp Tyr Trp Gly Gln Gly Val Met Val Thr
            100                 105                 110

Val Ser Ser Ala Lys Thr Thr Pro Pro Ser Val Tyr Pro Leu Ala Pro
        115                 120                 125

Gly Ser Ala Ala Gln Thr Asn Ser Met Val Thr Leu Gly Cys Leu Val
130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Thr Trp Pro Ser
            180                 185                 190

Glu Thr Val Thr Cys Asn Val Ala His Pro Ala Ser Ser Thr Lys Val
        195                 200                 205

Asp Lys Lys Ile Val Pro Arg Asp Cys Gly Cys Lys Pro Cys Ile Cys
210                 215                 220

Thr Val Pro Glu Val Ser Ser Val Phe Ile Phe Pro Pro Lys Pro Lys
225                 230                 235                 240

Asp Val Leu Thr Ile Thr Leu Thr Pro Lys Val Thr Cys Val Val Val
                245                 250                 255

Asp Ile Ser Lys Asp Asp Pro Glu Val Gln Phe Ser Trp Phe Val Asp
            260                 265                 270

Asp Val Glu Val His Thr Ala Gln Thr Gln Pro Arg Glu Glu Gln Phe
        275                 280                 285

Asn Ser Thr Phe Arg Ser Val Ser Glu Leu Pro Ile Met His Gln Asp
290                 295                 300

Trp Leu Asn Gly Lys Glu Phe Lys Cys Arg Val Asn Ser Ala Ala Phe
305                 310                 315                 320

Pro Ala Pro Ile Glu Lys Thr Ile Ser Lys Thr Lys Gly Arg Pro Lys
                325                 330                 335

Ala Pro Gln Val Tyr Thr Ile Pro Pro Pro Lys Glu Gln Met Ala Lys
            340                 345                 350

Asp Lys Val Ser Leu Thr Cys Met Ile Thr Asp Phe Phe Pro Glu Asp
        355                 360                 365
```

```
Ile Thr Val Glu Trp Gln Trp Asn Gly Gln Pro Ala Glu Asn Tyr Lys
        370             375             380

Asn Thr Gln Pro Ile Met Asp Thr Asp Gly Ser Tyr Phe Val Tyr Ser
385             390             395             400

Lys Leu Asn Val Gln Lys Ser Asn Trp Glu Ala Gly Asn Thr Phe Thr
            405             410             415

Cys Ser Val Leu His Glu Gly Leu His Asn His His Thr Glu Lys Ser
            420             425             430

Leu Ser His Ser Pro Gly
        435

<210> SEQ ID NO 19
<211> LENGTH: 219
<212> TYPE: PRT
<213> ORGANISM: Artificial Sequence
<220> FEATURE:
<223> OTHER INFORMATION: Synthetic construct

<400> SEQUENCE: 19

Asp Ile Val Met Thr Gln Thr Pro Val Ser Met Ser Val Ser Leu Gly
1               5                   10                  15

Gly Gln Val Ser Ile Ser Cys Arg Ser Ser Gln Ser Leu Val Asn Asn
            20                  25                  30

Asn Gly Asn Thr Tyr Leu Ser Trp Tyr Ile Gln Lys Pro Ser Gln Ser
        35                  40                  45

Pro Gln Leu Leu Ile Tyr Lys Val Ser Asn Arg Val Ser Gly Ile Ser
    50                  55                  60

Asp Arg Phe Ser Gly Ser Gly Ser Gly Thr Asp Phe Thr Leu Lys Ile
65                  70                  75                  80

Asn Lys Ile Glu Pro Asp Asp Leu Gly Val Tyr Tyr Cys Gly Gln Asn
                85                  90                  95

Thr Gln Tyr Pro Leu Thr Phe Gly Ser Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215
```

THERAPEUTIC USES FOR VEGFR1 ANTIBODIES

The present invention relates to the field of medicine. More particularly, the present invention relates to methods that may be useful for treating chronic kidney disease (CKD), and/or more particularly diabetic nephropathy (also known as diabetic kidney disease), in a patient with a VEGFR1 antibody.

Vascular endothelial growth factor receptor-1 (VEGFR-1, also known as Flt-1, SEQ ID NO: 1) is one of the three tyrosine kinase receptors (VEGFR1, VEGFR2, and VEGFR3) for VEGF family proteins. The VEGF family consists of a group of structurally related glycoproteins including VEGF-A, VEGF-B, VEGF-C, VEGF-D, and placental growth factor (P1GF). VEGF proteins play multiple biological and pathological roles by selectively binding to extracellular immunoglobulin-like domains of the three VEGF receptors. VEGF-A has high affinity for both VEGFR1 and VEGFR2, while VEGF-B and P1GF selectively bind to VEGFR1. VEGF-A/VEGFR2, as ligand and receptor respectively, play a major role in the signaling of vascular-angiogenic biological pathways. VEGFR1 and a soluble form of VEGFR1 (also known as sFlt-1) have been suggested by some groups to serve a decoy receptor role, sequestering VEGF-A, and preventing it from binding to its more pro-angiogenic partner, VEGFR2.

VEGF signaling is essential for vasculogenesis, angiogenesis, vascular homeostasis, inflammation, and therefore has been linked to several human diseases including cancer, diabetic complications, cardiovascular disease, and chronic inflammation. The VEGF system also plays a critical role in maintaining kidney function. While VEGF-A has been shown in some studies to have a protective effect on the kidney, the kidney has also been shown to be extremely sensitive to the effects of VEGF-A. Kidney injury has been shown to occur when VEGF-A levels are suppressed with a VEGF-A monoclonal antibody in humans (Eremina et al. (2008) NEJM 358:1129), and also when VEGF-A levels are elevated in mice over-expressing VEGF-A in the kidney glomerulus (Veron et al. (2010) Kidney Intl 77:989, and Hakroush et al. (2009) Am J Pathol 175:1883).

From biological studies of VEGF-A, treatment with VEGF-A has been suggested to likely be deleterious for patients with diabetes, atherosclerosis, or sepsis; these are all conditions that are either causes or complications of CKD. Increased VEGF-A levels have also been associated with diabetic nephropathy (Cha et al. (2000) Kidney Intl Supp 77:S104 and Hovind et al. (2000) Kidney Intl Supp 75:S56). Decreasing VEGF-A with VEGF-A antibodies was shown in a type 2 diabetes mouse model to improve glomerular hypertrophy and albuminuria, both markers for diabetic nephropathy (de Vriese et al. (2001) J AM Soc Nephol 12:993 and Flyvbjerg et al. (2002) Diabetes 51:3090).

sFlt-1 is a secreted form of VEGFR1 that arises from a splicing variant of the VEGFR1 gene. sFlt-1 has preserved ligand binding activity, and has been connected to the amount of VEGF-A that is available for signaling through VEGFR-2. The amount of active sFlt-1 in diabetic nephropathy has been studied, but the results have been inconsistent.

CKD is characterized by the progressive loss of kidney function. Diabetic nephropathy (also known as diabetic kidney disease) is one type of CKD, and is a chronic complication of diabetes mellitus. Increased albuminuria and gradual, progressive loss of renal function are primary manifestations in human diabetic nephropathy. Decreased renal function results in increased blood creatinine and blood urea nitrogen (BUN). Diabetes mellitus, hypertension, and glomerulonephritis are the most common causes of CKD. CKD patients experience over time an increase in albuminuria, proteinuria, serum creatinine, and renal histopathological lesions. Worsening CKD evolves into end stage renal disease (ERSD) for many patients, requiring either dialysis or kidney transplant. About 45% of ERSD patients have been estimated to have type 2 diabetes mellitus as the cause of their CKD. Glomerular filtration rate (GFR) is used to classify the severity of CKD for patients, with lower GFR corresponding to more severe CKD. Reducing the rate at which GFR declines in patients is expected to delay or prevent the development of ESRD. Angiotensin converting enzyme inhibitors or angiotensin II receptor antagonists are used as current standard of care to slow the progression of CKD to ERSD, but these have been shown inadequate to stop the ultimate progression to dialysis.

WO2006/055809 discloses the activity of VEGFR1 antibodies in multiple cancer xenograft models. Activity against certain non-neoplastic, angiogenic diseases, such as insulin-dependent diabetes mellitus and autoimmune nephritis, were also disclosed. However, to date, no antibody targeting VEGFR1 has been taught or suggested for therapeutic use for diabetic nephropathy or other forms of progressive CKD.

There remains a need to provide alternative methods to treat CKD. In particular, there remains a need to provide methods to treat diabetic nephropathy.

Accordingly, the present invention provides a method of treating chronic kidney disease in a patient, comprising administering to the patient an effective amount of a VEGFR1 antibody. In another embodiment, the present invention provides a method of treating chronic kidney disease in a patient, comprising administering to the patient an effective amount of a VEGFR1 antibody, wherein the chronic kidney disease is caused by diabetes mellitus. More particularly, the methods of the present invention provide for a patient at stage 3 or stage 4 of chronic kidney disease.

In an embodiment, the present invention provides a method of treating chronic kidney disease in a patient, comprising administering to a patient in need thereof, an effective amount of a VEGFR1 antibody, wherein the chronic kidney disease is diabetic nephropathy. In another embodiment, the present invention provides a method of treating chronic kidney disease in a patient, comprising administering to a patient in need thereof, an effective amount of a VEGFR1 antibody, wherein the chronic kidney disease is focal segmental glomerulosclerosis. In an embodiment, the present invention provides a method of treating chronic kidney disease in a patient, comprising administering to a patient in need thereof, an effective amount of a VEGFR1 antibody, wherein the chronic kidney disease is nephrotic syndrome.

In an embodiment, the present invention provides a method of decreasing proteinuria in a patient, comprising administering to a patient in need thereof, an effective amount of a VEGFR1 antibody. In a further embodiment, the present invention provides a method of decreasing proteinuria in a patient, comprising administering to a patient in need thereof, an effective amount of a VEGFR1 antibody, wherein the proteinuria is caused by chronic kidney disease. In a further embodiment, the present invention provides a method of decreasing proteinuria in a patient, comprising administering to a patient in need thereof, an effective amount of a VEGFR1 antibody, wherein the proteinuria is caused by diabetic nephropathy.

In an embodiment, the present invention provides a method of decreasing albuminuria in a patient, comprising administering to a patient in need thereof, an effective amount of a VEGFR1 antibody. In a further embodiment, the present invention provides a method of decreasing albuminuria in a patient, comprising administering to a patient in need thereof, an effective amount of a VEGFR1 antibody, wherein the albuminuria is caused by chronic kidney disease. In a further embodiment, the present invention provides a method of decreasing albuminuria in a patient, comprising administering to a patient in need thereof, an effective amount of a VEGFR1 antibody, wherein the albuminuria is caused by diabetic nephropathy.

In an embodiment, the present invention provides a method of decreasing the loss of glomerular filtration rate (GFR) reflected by an increase in serum creatinine in a patient, comprising administering to a patient in need thereof, an effective amount of a VEGFR1 antibody. In an embodiment, the present invention provides a method of protecting against renal histopathological lesions in a patient, comprising administering to a patient in need thereof, an effective amount of a VEGFR1 antibody.

In an embodiment, the present invention provides a method of slowing the rate of increase in blood urea nitrogen (BUN) in a patient, comprising administering to a patient in need thereof, an effective amount of a VEGFR1 antibody.

In an embodiment, the present invention provides a method of slowing the rate of progression to ESRD in a patient, comprising administering to a patient in need thereof, an effective amount of a VEGFR1 antibody. In an embodiment, the present invention provides a method of delaying progression to ESRD in a patient, comprising administering to a patient in need thereof, an effective amount of a VEGFR1 antibody, wherein the progression to ESRD is delayed at least 12 months. In an embodiment, the present invention provides a method of delaying progression to ESRD in a patient, comprising administering to a patient in need thereof, an effective amount of a VEGFR1 antibody, wherein the progression to ESRD is delayed at least 24 months. In an embodiment, the present invention provides a method of slowing the time to doubling of serum creatinine in a patient, comprising administering to a patient in need thereof, an effective amount of a VEGFR1 antibody. In an embodiment, the present invention provides a method of prolonging the time to a 30% reduction in GFR in a patient, comprising administering to a patient in need thereof, an effective amount of a VEGFR1 antibody.

In an embodiment, the present invention provides methods of decreasing free (unbound) sFLt-1, comprising administering to a patient in need thereof, an effective amount of a VEGFR1 antibody, wherein the patient has chronic kidney disease. In an embodiment, the present invention provides methods of decreasing the ability of sFLt-1 to signal and/or bind other proteins, comprising administering to a patient in need thereof, an effective amount of a VEGFR1 antibody, wherein the patient has chronic kidney disease.

In an embodiment, the present invention provides a VEGFR1 antibody for use in the treatment of chronic kidney disease. In a further embodiment, the present invention provides a VEGFR1 antibody for use in the treatment of chronic kidney disease, wherein the chronic kidney disease is caused by diabetes mellitus. More particularly, the present invention provides a VEGFR1 antibody for use in the treatment of chronic kidney disease, wherein the chronic kidney disease is at stage 3 or stage 4.

In an embodiment, the present invention provides a VEGFR1 antibody for use in the treatment of chronic kidney disease, wherein the chronic kidney disease is diabetic nephropathy. In another embodiment, the present invention provides a VEGFR1 antibody for use in the treatment of chronic kidney disease, wherein the chronic kidney disease is focal segmental glomerulosclerosis. In another embodiment, the present invention provides a VEGFR1 antibody for use in the treatment of chronic kidney disease, wherein the chronic kidney disease is nephrotic syndrome.

In an embodiment, the present invention provides a VEGFR1 antibody for use in decreasing proteinuria. In a further embodiment, the present invention provides a VEGFR1 antibody for use in decreasing proteinuria, wherein the proteinuria is caused by chronic kidney disease. In a further embodiment, the present invention provides a VEGFR1 antibody for use in decreasing proteinuria, wherein the proteinuria is caused by diabetic nephropathy.

In an embodiment, the present invention provides a VEGFR1 antibody for use in decreasing albuminuria. In a further embodiment, the present invention provides a VEGFR1 antibody for use in decreasing albuminuria, wherein the albuminuria is caused by diabetic nephropathy. In a further embodiment, the present invention provides a VEGFR1 antibody for use in decreasing albuminuria, wherein the albuminuria is caused by diabetic nephropathy.

In an embodiment, the present invention provides a VEGFR1 antibody for use in decreasing the loss of glomerular filtration rate (GFR) reflected by an increase in serum creatinine. In an embodiment, the present invention provides a VEGFR1 antibody for use in protecting against renal histopathological lesions.

In an embodiment, the present invention provides a VEGFR1 antibody for use in slowing the rate of increase in blood urea nitrogen (BUN).

In an embodiment, the present invention provides a VEGFR1 antibody for use in slowing the rate of progression to ESRD. In an embodiment, the present invention provides a VEGFR1 antibody for use in delaying progression to ESRD, wherein the progression to ESRD is delayed at least 12 months. In an embodiment, the present invention provides a VEGFR1 antibody for use in delaying progression to ESRD, wherein the progression to ESRD is delayed at least 24 months. In an embodiment, the present invention provides a VEGFR1 antibody for use in slowing the time to doubling of serum creatinine. In an embodiment, the present invention provides a VEGFR1 antibody for use in prolonging the time to a 30% reduction in GFR.

In an embodiment, the present invention provides a VEGFR1 antibody for use in decreasing free (unbound) sFLt-1. In an embodiment, the present invention provides a VEGFR1 antibody for use in decreasing the ability of sFLt-1 to signal and/or bind other proteins.

In an embodiment, the present invention provides the use of a VEGFR1 antibody for the manufacture of a medicament for the treatment of chronic kidney disease. In an embodiment, the present invention provides the use of a VEGFR1 antibody for the manufacture of a medicament for the treatment of chronic kidney disease, wherein the chronic kidney disease is caused by diabetes mellitus. More particularly, the present invention provides the use of a VEGFR1 antibody for the manufacture of a medicament for the treatment of chronic kidney disease, wherein the chronic kidney disease is at stage 3 or stage 4.

In an embodiment, the present invention provides the use of a VEGFR1 antibody for the manufacture of a medicament for the treatment of chronic kidney disease, wherein the chronic kidney disease is diabetic nephropathy. In another embodiment, the present invention provides the use of a VEGFR1 antibody for the manufacture of a medicament for the treatment of chronic kidney disease, wherein the chronic kidney disease is focal segmental glomerulosclerosis. In another embodiment, the present invention provides the use of a VEGFR1 antibody for the manufacture of a medicament for the treatment of chronic kidney disease, wherein the chronic kidney disease is nephrotic syndrome.

In an embodiment, the present invention provides the use of a VEGFR1 antibody for the manufacture of a medicament for decreasing proteinuria. In a further embodiment, the present invention provides the use of a VEGFR1 antibody for the manufacture of a medicament for decreasing proteinuria, wherein the proteinuria is caused by chronic kidney disease. In a further embodiment, the present invention provides the use of a VEGFR1 antibody for the manufacture of a medicament for decreasing proteinuria, wherein the proteinuria is caused by diabetic nephropathy.

In an embodiment, the present invention provides the use of a VEGFR1 antibody for the manufacture of a medicament for decreasing albuminuria. In a further embodiment, the present invention provides the use of a VEGFR1 antibody for the manufacture of a medicament for decreasing albuminuria, wherein the albuminuria is caused by chronic kidney disease. In a further embodiment, the present invention provides the use of a VEGFR1 antibody for the manufacture of a medicament for decreasing albuminuria, wherein the albuminuria is caused by diabetic nephropathy.

In an embodiment, the present invention provides the use of a VEGFR1 antibody for the manufacture of a medicament for decreasing the loss of glomerular filtration rate (GFR) reflected by an increase in serum creatinine. In an embodiment, the present invention provides the use of a VEGFR1 antibody for the manufacture of a medicament for protecting against renal histopathological lesions.

In an embodiment, the present invention provides the use of a VEGFR1 antibody for the manufacture of a medicament for slowing the rate of increase in blood urea nitrogen (BUN).

In an embodiment, the present invention provides the use of a VEGFR1 antibody for the manufacture of a medicament for slowing the rate of progression to ESRD. In an embodiment, the present invention provides the use of a VEGFR1 antibody for the manufacture of a medicament for delaying progression to ESRD, wherein the progression to ESRD is delayed at least 12 months. In an embodiment, the present invention provides the use of a VEGFR1 antibody for the manufacture of a medicament for delaying progression to ESRD, wherein the progression to ESRD is delayed at least 24 months. In an embodiment, the present invention provides the use of a VEGFR1 antibody for the manufacture of a medicament for slowing the time to doubling of serum creatinine. In an embodiment, the present invention provides the use of a VEGFR1 antibody for the manufacture of a medicament for prolonging the time to a 30% reduction in GFR.

In an embodiment, the present invention provides the use of a VEGFR1 antibody for the manufacture of a medicament for decreasing free (unbound) sFLt-1. In an embodiment, the present invention provides the use of a VEGFR1 antibody for the manufacture of a medicament for decreasing the ability of sFLt-1 to signal and/or bind other proteins.

The present invention also provides a method of treating chronic kidney disease in a patient, comprising administering VEGFR1 antibodies, as described herein, in simultaneous or sequential combination with a standard of care. The present invention also provides VEGFR1 antibodies for use in the treatment of chronic kidney disease, comprising administering simultaneous or sequential combination with a standard of care.

The present invention also provides a method of treating diabetic nephropathy in a patient, comprising administering VEGFR1 antibodies, as described herein, in simultaneous or sequential combination with a standard of care. The present invention also provides VEGFR1 antibodies for use in the treatment of diabetic nephropathy, comprising administering simultaneous or sequential combination with a standard of care. Standard of care includes, and not limited to, angiotensin converting enzyme (ACE) inhibitors or angiotensin II receptor (ARB) antagonists.

The VEGFR1 antibodies as described and used herein may be administered in simultaneous or sequential combination with a standard of care. Standard of care includes, and not limited to, angiotensin converting enzyme (ACE) inhibitors or angiotensin II receptor (ARB) antagonists.

In an embodiment, the methods and uses of the present invention comprise a VEGFR1 antibody wherein the VEGFR1 antibody has a $K_D$ for VEGFR1 of less than 80 pM as determined by surface plasmon resonance at 25° C. The Kd values are established by a binding equilibrium at 25° C. as described in Example 2. In an embodiment, the methods and uses of the present invention comprise a VEGFR1 antibody wherein the VEGFR1 antibody neutralizes VEGF-A binding in vitro to VEGFR1 with an $IC_{50}$ less than 2.0 nM. In an embodiment, the methods and uses of the present invention comprise a VEGFR1 antibody wherein the VEGFR1 antibody neutralizes P1GF binding in vitro to VEGFR1 with an $IC_{50}$ less than 2.0 nM. The neutralization values are established as described in Example 4 (see Table 4b). In an embodiment, the methods and uses of the present invention comprise a VEGFR1 antibody wherein the VEGFR1 antibody has a $K_D$ for VEGFR1 of less than 80 pM as determined by surface plasmon resonance at 25° C., neutralizes VEGF-A binding in vitro to VEGFR1 with an $IC_{50}$ less than 2.0 nM, and/or antibody neutralizes P1GF binding in vitro to VEGFR1 with an IC50 less than 2.0 nM.

In an embodiment, the present invention provides methods of treatment, comprising administering to a patient in need thereof, an effective amount of a VEGFR1 antibody, wherein the patient has an increase in VEGFR2 phosphorylation. In an embodiment, the present invention provides methods of treatment, comprising administering to a patient in need thereof, an effective amount of a VEGFR1 antibody, wherein the patient has an increase in P1GF levels. In an embodiment, the present invention provides methods of treatment, comprising administering to a patient in need thereof, an effective amount of a VEGFR1 antibody, wherein the patient has an increase in VEGF-A levels. In an embodiment, the present invention provides methods of treatment, comprising administering to a patient in need thereof, an effective amount of a VEGFR1 antibody, wherein the patient has an increase in sFLt-1 levels. In an embodiment, the present invention provides methods of treatment, comprising administering to a patient in need thereof, an effective amount of a VEGFR1 antibody, wherein the patient has an increase in VEGF-B levels. In embodiments, the present invention provides methods of treatment, wherein the P1GF levels, VEGF-A levels, sFLt-1 levels, and VEGF-B levels are measured by ELISA.

In an embodiment, the present invention provides a VEGFR1 antibody for use when VEGFR2 phosphorylation is increased. In an embodiment, the present invention provides a VEGFR1 antibody for use when PLGF levels are increased. In an embodiment, the present invention provides a VEGFR1 antibody for use when VEGF-A levels are increased. In an embodiment, the present invention provides a VEGFR1 antibody for use when sFLt-1 levels are increased. In an embodiment, the present invention provides a VEGFR1 antibody for use when VEGF-B levels are increased. In embodiments, the present invention provides a VEGFR1 antibody for uses wherein the P1GF levels, VEGF-A levels, sFLt-1 levels, and VEGF-B levels are measured by ELISA.

The present invention provides a VEGFR1 antibody which is believed to cause a reduction in proteinuria with a concomitant reduction in disease progression in humans. Further, the present invention provides a VEGFR1 antibody which is believed to be effective in the treatment of chronic kidney disease in humans. Further, the present invention provides a VEGFR1 antibody which is believed to be effective in the treatment of diabetic nephropathy in humans. The present invention provides a VEGFR1 antibody which is believed to cause a reduction in albuminuria with a concomitant reduction in disease progression in humans. The present invention provides a VEGFR1 antibody which is believed to cause a reduction in serum creatinine with a concomitant reduction in disease progression in humans.

In an embodiment, the methods and uses of the present invention comprise a preferred VEGFR1 antibody wherein the VEGFR1 antibody is an antibody comprising a light chain variable region (LCVR) and a heavy chain variable region (HCVR), wherein the LCVR comprises the complementarity determining regions (CDRs) LCDR1, LCDR2, and LCDR3, and the HCVR comprises the CDRs HCDR1, HCDR2, and HCDR3, wherein the LCDR1 is the polypeptide of RASQSVSSSYLA (SEQ ID NO: 8), the LCDR2 is the polypeptide of GASSRAT (SEQ ID NO: 9), the LCDR3 is the polypeptide of QQYGSSPLT (SEQ ID NO: 10), the HCDR1 is the polypeptide of GFAFSSYGMH (SEQ ID NO: 2), the HCDR2 is the polypeptide of VIWYDGSNKYY-ADSVRG (SEQ ID NO: 3), and the HCDR3 is the polypeptide of DHYGSGVHHYFYYGLDV (SEQ ID NO: 4).

In an embodiment, the methods and uses of the present invention comprise a preferred VEGFR1 antibody wherein the VEGFR1 antibody is an antibody comprising a light chain variable region (LCVR) and a heavy chain variable region (HCVR), and wherein the LCVR is the polypeptide of SEQ ID NO: 11, and the HCVR is the polypeptide of SEQ ID NO: 5.

In an embodiment, the methods and uses of the present invention comprise a preferred VEGFR1 antibody wherein the VEGFR1 antibody comprises a light chain (LC) and a heavy chain (HC), wherein the LC is the polypeptide of SEQ ID NO: 12, and the HC is the polypeptide of SEQ ID NO: 6. In another embodiment, the methods and uses of the present invention comprise a VEGFR1 antibody wherein the VEGFR1 antibody comprises a light chain (LC) and a heavy chain (HC), wherein the LC is the polypeptide of SEQ ID NO: 12, and the HC is the polypeptide of SEQ ID NO: 7.

In an embodiment, the methods and uses of the present invention comprise a preferred VEGFR1 antibody wherein the VEGFR1 antibody comprises two light chains and two heavy chains, wherein each light chain is the polypeptide of SEQ ID NO: 12, and each heavy chain is the polypeptide of SEQ ID NO: 6. In another embodiment, the methods and uses of the present invention comprise a preferred VEGFR1 antibody wherein the VEGFR1 antibody comprises two light chains and two heavy chains, wherein each light chain is the polypeptide of SEQ ID NO: 12, and each heavy chain is the polypeptide of SEQ ID NO: 7.

In an embodiment, the present invention provides a method of treating chronic kidney disease in a patient, comprising administering to a patient in need thereof, an effective amount of a VEGFR1 antibody, wherein the VEGFR1 antibody comprises two light chains and two heavy chains, wherein each light chain is the polypeptide of SEQ ID NO: 12, and each heavy chain is the polypeptide of SEQ ID NO: 6. In another embodiment, the present invention provides a method of treating chronic kidney disease in a patient, comprising administering to a patient in need thereof, an effective amount of a VEGFR1 antibody, wherein the VEGFR1 antibody comprises two light chains and two heavy chains, wherein each light chain is the polypeptide of SEQ ID NO: 12, and each heavy chain is the polypeptide of SEQ ID NO: 7.

In an embodiment, the present invention provides a method of treating chronic kidney disease in a patient, comprising administering to a patient in need thereof, an effective amount of a VEGFR1 antibody, wherein the chronic kidney disease is diabetic nephropathy, and wherein the VEGFR1 antibody comprises two light chains and two heavy chains, wherein each light chain is the polypeptide of SEQ ID NO: 12, and each heavy chain is the polypeptide of SEQ ID NO: 6. In another embodiment, the present invention provides a method of treating chronic kidney disease in a patient, comprising administering to a patient in need thereof, an effective amount of a VEGFR1 antibody, wherein the chronic kidney disease is diabetic nephropathy, and wherein the VEGFR1 antibody comprises two light chains and two heavy chains, wherein each light chain is the polypeptide of SEQ ID NO: 12, and each heavy chain is the polypeptide of SEQ ID NO: 7.

In an embodiment, the present invention provides a method of treating chronic kidney disease in a patient, comprising administering to a patient in need thereof, an effective amount of a VEGFR1 antibody, wherein the chronic kidney disease is focal segmental glomerulosclerosis, and wherein the VEGFR1 antibody comprises two light chains and two heavy chains, wherein each light chain is the polypeptide of SEQ ID NO: 12, and each heavy chain is the polypeptide of SEQ ID NO: 6. In another embodiment, the present invention provides a method of treating chronic kidney disease in a patient, comprising administering to a patient in need thereof, an effective amount of a VEGFR1 antibody, wherein the chronic kidney disease is focal segmental glomerulosclerosis, and wherein the VEGFR1 antibody comprises two light chains and two heavy chains, wherein each light chain is the polypeptide of SEQ ID NO: 12, and each heavy chain is the polypeptide of SEQ ID NO: 7.

In an embodiment, the present invention provides a VEGFR1 antibody for use in the treatment of chronic kidney disease, wherein the VEGFR1 antibody comprises two light chains and two heavy chains, wherein each light chain is the polypeptide of SEQ ID NO: 12, and each heavy chain is the polypeptide of SEQ ID NO: 6. In another embodiment, the present invention provides a VEGFR1 antibody for use in the treatment of chronic kidney disease, wherein the VEGFR1 antibody comprises two light chains and two heavy chains, wherein each light chain is the polypeptide of SEQ ID NO: 12, and each heavy chain is the polypeptide of SEQ ID NO: 7.

In an embodiment, the present invention provides a VEGFR1 antibody for use in the treatment of chronic kidney disease, wherein the chronic kidney disease is diabetic nephropathy, and wherein the VEGFR1 antibody comprises two light chains and two heavy chains, wherein each light chain is the polypeptide of SEQ ID NO: 12, and each heavy chain is the polypeptide of SEQ ID NO: 6. In another embodiment, the present invention provides a VEGFR1 antibody for use in the treatment of chronic kidney disease, wherein the chronic kidney disease is diabetic nephropathy, and wherein the VEGFR1 antibody comprises two light chains and two heavy chains, wherein each light chain is the polypeptide of SEQ ID NO: 12, and each heavy chain is the polypeptide of SEQ ID NO: 7.

In an embodiment, the present invention provides a VEGFR1 antibody for use in the treatment of chronic kidney disease, wherein the chronic kidney disease is focal segmental glomerulosclerosis, and wherein the VEGFR1 antibody comprises two light chains and two heavy chains, wherein each light chain is the polypeptide of SEQ ID NO: 12, and each heavy chain is the polypeptide of SEQ ID NO: 6. In another embodiment, the present invention provides a VEGFR1 antibody for use in the treatment of chronic kidney disease, wherein the chronic kidney disease is focal segmental glomerulosclerosis, and wherein the VEGFR1 antibody comprises two light chains and two heavy chains, wherein each light chain is the polypeptide of SEQ ID NO: 12, and each heavy chain is the polypeptide of SEQ ID NO: 7.

The present invention further provides a method of treating chronic kidney disease in a patient, comprising administering to the patient an effective amount of a VEGFR1 antagonist.

Preferably, the VEGFR1 antagonist is a VEGFR1 antibody.

The general structure of an "antibody" is very well-known in the art. For an antibody of the IgG type, there are four amino acid chains (two "heavy" chains and two "light" chains) that are cross-linked via intra- and inter-chain disulfide bonds. For an antibody, one of the heavy chains forms an inter-chain disulfide bond with one of the light chains, and the other heavy chain forms an inter-chain disulfide bond with the other light chain, and one of the heavy chains forms two inter-chain disulfide bonds with the other heavy chain.

When expressed in certain biological systems, antibodies having human Fc sequences which are glycosylated in the Fc region. Antibodies may be glycosylated at other positions as well. One of skill in the art will appreciate that antibodies of the present invention may contain such glycosylation. Typically, glycosylation occurs in the Fc region of the antibody at a highly conserved N-glycosylation site. N-glycans typically attach to asparagines.

Antibody I comprises two light chains and two heavy chains, wherein each of the light chains consists of the polypeptide of SEQ ID NO: 12 and each of the heavy chains consists of the polypeptide of SEQ ID NO: 6. Antibody II comprises two light chains and two heavy chains, wherein each of the light chains consists of the polypeptide of SEQ ID NO: 12 and each of the heavy chains consists of the polypeptide of SEQ ID NO: 7. A particular DNA molecule encoding each of the heavy chains of Antibody I is SEQ ID NO: 13, and a particular DNA molecule encoding each of the light chains of Antibody I is SEQ ID NO: 15. A particular DNA molecule encoding each of the heavy chains of Antibody II is SEQ ID NO: 14, and a particular DNA molecule encoding each of the light chains of Antibody II is SEQ ID NO: 15.

Antibody I and Antibody II are antibodies against human VEGFR1; Antibody I has a IgG1 Fc, and Antibody II has a IgG4 Fc. Antibody III is a rat IgG1 antibody against mouse VEGFR1, and Antibody IV is a chimeric antibody against mouse VEGFR1 with a rat variable region and a mouse IgG1 Fc.

An antibody for the methods and uses of the present invention can be produced using techniques well known in the art, e.g., recombinant technologies, phage display technologies, synthetic technologies, or combinations of such technologies or other technologies readily known in the art. Methods for producing and purifying antibodies are well known in the art and can be found, for example, in Harlow and Lane (1988) *Antibodies, A Laboratory Manual*, Cold Spring Harbor Laboratory Press, Cold Spring Harbor, N.Y., chapters 5-8 and 15, ISBN 0-87969-314-2.

"Effective amount" means the amount of an antibody for the methods and uses of the present invention or pharmaceutical composition comprising an antibody for the methods and uses of the present invention that will elicit the biological or medical response of or desired therapeutic effect on a tissue, system, animal, mammal or human that is being sought by the researcher, medical doctor, or other clinician. An effective amount of the antibody may vary according to factors such as the disease state, age, sex, and weight of the individual, and the ability of the antibody to elicit a desired response in the individual. An effective amount is also one in which any toxic or detrimental effect of the antibody is outweighed by the therapeutically beneficial effects. The effective amount can comprise an amount of about 0.001 to 20 mg/kg per single (e.g., bolus), multiple or continuous administration. In some instances, dosage levels below the lower limit of the aforesaid range may be more than adequate, while in other cases still larger doses may be employed.

The terms "treatment," "treat," "treating," and the like, are meant to include slowing or reversing the progression of a disorder. These terms also include alleviating, ameliorating, attenuating, eliminating, or reducing one or more symptoms of a disorder or condition, even if the disorder or condition is not actually eliminated and even if progression of the disorder or condition is not itself slowed or reversed. A patient refers to a mammal, preferably a human with a disease, disorder or condition that would benefit from inhibition of VEGFR1 activity.

Stage 3 or 4 of CKD has been defined to be a patient with an estimated GFR (eGFR) of between 15 and 59 ml/min/1.73 m$^2$. Others do not use a stage definition for CKD patients, but rather define patients by their eGFR as follows: normal>80, mild 50-80, moderate 30-50, and severe<30.

An antibody for the methods and uses of the present invention, or pharmaceutical composition comprising the same, may be administered by parenteral routes (e.g., subcutaneous, intravenous, intraperitoneal, intramuscular, or transdermal). An antibody for the methods and uses of the present invention may be administered to a patient alone or in combination with a pharmaceutically acceptable carrier and/or diluent in single or multiple doses. Pharmaceutical compositions for the methods and uses of the present invention can be prepared by methods well known in the art (e.g., *Remington: The Science and Practice of Pharmacy*, 19$^{th}$ ed. (1995), A. Gennaro et al., Mack Publishing Co.) and comprise an antibody, as disclosed herein, and one or more pharmaceutically acceptable carriers, diluents, or excipients.

EXAMPLE 1

Antibody Expression and Purification

The polypeptides of the variable regions of the heavy chain and light chain, the complete heavy chain and light chain amino acid sequences of Antibody I-IV, and the nucleotide sequences encoding the same, are listed below in the section entitled "Amino Acid and Nucleotide Sequences." In addition, the light chain and heavy chain CDR polypeptides are shown in Table 1.

The VEGFR1 antibodies for the methods and uses of the present invention, including, but not limited to, Antibodies I and II, can be made and purified essentially as follows. An appropriate host cell, such as HEK 293 EBNA or CHO, can be either transiently or stably transfected with an expression system for secreting antibodies using an optimal predetermined HC:LC vector ratio or a single vector system encoding both HC and LC. Clarified media, into which the antibody has been secreted, may be purified using any of many commonly-used techniques. For example, the medium may be conveniently applied to a MabSelect column (GE Healthcare), or KappaSelect column (GE Healthcare) for Fab fragment, that has been equilibrated with a compatible buffer, such as phosphate buffered saline (pH 7.4). The column may be washed to remove nonspecific binding components. The bound antibody may be eluted, for example, by pH gradient (such as 20 mM Tris buffer pH 7 to 10 mM sodium citrate buffer pH 3.0, or phosphate buffered saline pH 7.4 to 100 mM glycine buffer pH 3.0). Antibody fractions may be detected, such as by SDS-PAGE, and then may be pooled. Further purification is optional, depending on the intended use. The antibody may be concentrated and/or sterile filtered using common techniques. Soluble aggregate and multimers may be effectively removed by common techniques, including size exclusion, hydrophobic interaction, ion exchange, multimodal, or hydroxyapatite chromatography. The product may be immediately frozen at −70° C. or may be lyophilized.

BIAcore® 3000, or a BIAcore® T100 (GE HealthCare) according to methods known in the art. Binding kinetics, affinity, and specificity may be used in the analysis to demonstrate that the disclosed antibodies to mouse VEGFR1 function similarly in vitro to the disclosed antibodies to human VEGFR1.

Binding affinity, specificity, kinetics and stoichiometry of the antibodies to various species of VEGF receptors may be determined using a SPR assay on a Biacore instrument primed with HBS-EP running buffer (GE Healthcare #BR-1006-69) and analysis temperature may be set at either 25° C. or 37° C. A CM4 chip (S series for the T100 at 37° C.) containing immobilized goat anti-(human or mouse) kappa (κ chain specific) or protein A may be generated using standard NHS-EDC amine coupling on two or all four flow cells (Fc) and used to employ a capture methodology. Antibody samples or VEGF-Fc receptors may be prepared at a concentration range between 1 and 10 μg/mL by dilution into running buffer. VEGFR1-His, Antibody II or Antibody IV may be prepared at different concentrations (concentration range of 200 nM to 0.078 nM in 2-fold dilution increments). Each analysis cycle may consist of (1) capturing antibody samples on immobilized protein A or anti-(human or mouse) kappa (κ chain specific) on separate flow cells (Fc2, Fc3, and Fc4), (2) injection of 250 μL (300-sec) of His-tagged receptor, Antibody II-Fab or Antibody IV over all Fc at 50 μL/min, (3) return to buffer flow for 20 min to monitor dissociation phase, (4) regeneration of chip surfaces with a 25 μL (30-sec) injection of glycine, pH 1.5, (5) equilibration of chip surfaces with a 25 μL (30-sec) injection of HBS-EP. Data may be processed using standard double-referencing and fit to a 1:1 binding model using Biacore evaluation software, version 4.1 for Biacore 2000 and 2.0.3

TABLE 1

| | SEQ ID NOs | | | |
|---|---|---|---|---|
| Antibody | Light Chain | Heavy Chain | LCVR | HCVR |
| I | 12 | 6 | 11 | 5 |
| II | 12 | 7 | 11 | 5 |
| III | 17 | 16 | | |
| IV | 19 | 18 | | |

| Antibody | LCDR1 | LCDR2 | LCDR3 |
|---|---|---|---|
| I | RASQSVSSSYLA (SEQ ID NO: 8) | GASSRAT (SEQ ID NO: 9) | QQYGSSPLT (SEQ ID NO: 10) |
| II | RASQSVSSSYLA (SEQ ID NO: 8) | GASSRAT (SEQ ID NO: 9) | QQYGSSPLT (SEQ ID NO: 10) |

| Antibody | HCDR1 | HCDR2 | HCDR3 |
|---|---|---|---|
| I | GFAFSSYGMH (SEQ ID NO: 2) | VIWYDGSNKYYADSVRG (SEQ ID NO: 3) | DHYGSGVHHYFYYGLDV (SEQ ID NO: 4) |
| II | GFAFSSYGMH (SEQ ID NO: 2) | VIWYDGSNKYYADSVRG (SEQ ID NO: 3) | DHYGSGVHHYFYYGLDV (SEQ ID NO: 4) |

EXAMPLE 2

Binding Kinetics, Affinity, and Specificity of VEGFR1 Antibodies

The binding kinetics, affinity, and selectivity to human VEGFR1, as well as human VEGFR2 and human VEGFR3, for antibodies for the methods and uses of the present invention, may be determined by use of a surface plasmon resonance (SPR) biosensor such as a BIAcore® 2000, for Biacore T100, to determine the association rate ($k_{on}$, $M^{-1}s^{-1}$ units), dissociation rate ($k_{off}$, $s^{-1}$ units), and $R_{max}$ (RU units). The equilibrium dissociation constant ($K_D$) may be calculated from the relationship $K_D = k_{off}/k_{on}$.

In experiments performed essentially as described in this Example 2, Antibodies I, II, III, and IV bind their corresponding species of VEGFR1 with similarly high binding affinity ($K_D$) (see Table 2). Antibodies II and IV both show good selectivity for VEGFR1 by not binding to VEGFR2 and VEGFR3 up to 200 nM of receptor. Antibody II has tight picomolar affinity for human and cynomolgus VEGFR1 receptors. The $K_D$ of Antibody II for human VEGFR1 is 740+/−34 pM (n=3) at 37° C. and 554+/−29 pM (n=3) for cynomolgus VEGFR1 at 37° C.

To perform the internalization assay, transduced BaF3 cells may be washed three times with 20 mL of culture medium without IL-3 to wash out IL-3. 100 µl of cells in culture medium without IL-3 may be added to each well of

TABLE 2

In vitro binding parameters of Antibodies I, II, III, and IV to various species of VEGFR1, VEGFR2 or VEGFR3 receptors, using surface plasmon resonance (SPR)

| Antibody | Receptor | Species | n | Temp (° C.) | $k_{on}$, 1/M 1/s | $k_{off}$, 1/s | $K_d$, pM (a) |
|---|---|---|---|---|---|---|---|
| Ab I | VEGFR1 | Human | 3 | 25 | (4.08 +/− 1.50) × $10^5$ | (1.00 +/− 0.01) × $10^{-5}$ | ≤26 +/− 8.0 |
| Ab II | VEGFR1 | Human | 6 | 25 | (4.87 +/− 2.29) × $10^5$ | (1.42 +/− 1.0) × $10^{-5}$ | ≤42 +/− 29 |
|  |  | Human | 3 | 37 | (3.25 +/− 0.03) × $10^5$ | (2.40 +/− 0.10) × $10^{-4}$ | 740 +/− 34 |
|  |  | Cynomolgus | 3 | 37 | (1.49 +/− 0.04) × $10^5$ | (8.30 +/− 0.63) × $10^{-5}$ | 554 +/− 29 |
|  |  | Mouse | 1 | 25 | nd | nd | nd |
|  | VEGFR2 | Human | 1 | 25 | nd | nd | nd |
|  |  | Mouse | 1 | 25 | nd | nd | nd |
|  | VEGFR3 | Human | 1 | 25 | nd | nd | nd |
|  |  | Mouse | 1 | 25 | nd | nd | nd |
| Ab III | VEGFR1 | Mouse | 1 | 25 | 5.77 × $10^5$ | 1.87 × $10^{-5}$ | 32 |
| Ab IV | VEGFR1 | Human | 1 | 25 | nd | nd | nd |
|  |  | Mouse | 4 | 25 | (5.24 +/− 0.98) × $10^5$ | <1.0 × $10^{-5g}$ | ≤18 +/− 4 |
|  | VEGFR2 | Human | 1 | 25 | nd | nd | nd |
|  |  | Mouse | 1 | 25 | nd | nd | nd |
|  | VEGFR3 | Human | 1 | 25 | nd | nd | nd |
|  |  | Mouse | 1 | 25 | nd | nd | nd |

(a) calculated as $K_D = k_{off}/k_{on}$ from each individual experiment and the final value is obtained by averaging several independent $K_D$ values.
nd = not determined because no binding was observed up to ~200 nM concentration of the receptors

EXAMPLE 3

Internalization of VEGFR1 by Antibody II and Antibody IV in Cultured Cells Expressing Chimeric Human VEGFR1/EpoR or Mouse VEGFR1/mouseEpoR Receptor The ability of VEGFR1 antibodies to internalize, and subsequently degrade, VEGFR1 can be determined by measuring internalization of VEGFR1 in cells expressing chimeric mouse VEGFR1/mouse EpoR or human VEGFR1/ mouse EpoR receptor. VEGFR1 internalization may be used in the analysis to demonstrate that the disclosed antibodies to mouse VEGFR1 function similarly in vitro to the disclosed antibodies to human VEGFR1. BaF3 cells survive in the absence of IL-3 when expressing the chimeric VEGFR1/ Epo receptors. Decreasing cell surface chimeric VEGFR1/ EpoR by antibody mediated internalization results in cell death.

Human and mouse VEGFR1 extracellular domain and trans-membrane domain may be fused with intracellular domain of Epo receptor. The chimeric receptors may be cloned into pMSCV puro retroviral vector (Clontech, catalog number 634401). BaF3-mouseVEGFR1-mouseEpoR cells and BaF3-humanVEGFR1-mouseEpoR cells may be generated by retrovirus infection. The retrovirus may be produced by transfecting Phoenix Eco retroviral packaging cells (ATCC) with mouse VEGFR1/mouseEpoR or human-VEGFR1/mouseEpoR respectively. The retroviral particles may be used to transduce BaF3 cells. The BaF3-VEGFR1-EpoR cells may be cultured in RPMI-1640 (Thermo Scientific, #SH30255.01), 10% (v/v) FBS (Invitrogen, #10082), 1 mM sodium pyruvate (Thermo Scientific, #SH30239.01), 100 U/500 mL penicillin G, and 100 µg/500 mL streptomycin (Thermo Scientific, #SV30079.01), 2 µg/mL puromycin (Calbiochem #540411); 5 ng/mL murine IL-3 (R & D #403-ML-CF).

white/clear 96-well tissue culture plates (BD #353377) to achieve 1-2×$10^4$ cells/well. VEGFR1 and isotype control antibodies may be serially diluted with culture medium without IL-3 to achieve 2× the final concentrations to be tested, and then 100 µl of the 2× antibody solutions may be added to each well. The plates may then be incubated at 37° C. under 95% relative humidity and 5% (v/v) $CO_2$. After culture for six days, the number of viable cells may be determined by CellTiter-Glo Luminescent Cell Viability Assay (Promega #G7571). The plates and CellTiter-Glo substrates may be equilibrated to room temperature for 30 minutes. 100 µl of CellTiter-Glo may be added to each well. The plates may be shaken for 2 minutes on an orbital shaker to mix contents and continued to incubate at room temperature for 10 minutes to stabilize luminescent signal. The luminescence may be recorded by a Wallac Victor3™ 1420 Multilable Counter (PerkinElmer Precisely). The percentage of cell variability in VEGFR1 and control IgG antibodies treated groups may be calculated by comparing to BaF3 cells without antibody treatment. The average of triplicate treatments of each dose may be used as mean and for standard error calculation. T-test may be used to compare data between VEGFR1 and control antibodies at same doses. A P value of less than 0.05 may be considered as statistical significant.

In experiments performed essentially as described in this Example 3, with incubation of different doses of Antibody II, the antibody inhibits BaF3-mouseVEGFR1-mouseEpoR cell proliferation as exhibited by the significant decrease in viability compared to human IgG4 control antibody (Table 3). Similarly, after six days of incubation with different dose of Antibody IV, the BaF3-mouse VEGFR1-mouse EpoR cells showed more cell death as compared to mouse IgG1 control antibody (Table 3). These results demonstrate internalization of the cell surface VEGFR1 receptor by both Antibody II and IV. Furthermore, the results indicate that the binding of Antibody II and IV to the chimeric VEGFR1 on BaF3 cells does not stimulate receptor activation and cell proliferation.

TABLE 3

Antibody II and IV decrease cell viability in BaF3 cells expressing chimeric mouse and human VEGFR1/EpoR

| | 0.0003 | 0.001 | 0.006 | 0.03 | 0.16 | 0.8 | 4 | 20 | 100 |
|---|---|---|---|---|---|---|---|---|---|
| | Antibody II (nM) | | | | | | | | |
| Cell viability (%) | 88.02 +/− 7.06 | 95.30 +/− 6.09 | 74.62 +/− 4.17 | 59.24 +/− 8.78 | 35.75 +/− 1.22 | 33.22 +/− 5.28 | 34.28 +/− 1.77 | 23.35 +/− 2.23 | 26.53 +/− 2.85 |
| | Antibody IV (nM) | | | | | | | | |
| Cell viability (%) | 97.50 +/− 6.88 | 108.28 +/− 19.14 | 93.9 +/− 8.21 | 84.37 +/− 3.61 | 54.77 +/− 7.21 | 13.29 +/− 1.66 | 7.17 +/− 1.05 | 4.28 +/− 0.35 | 2.60 +/− 0.37 |

Data displays the average and standard error of triplicate treatments and is representative of two experiments.

EXAMPLE 4

Neutralization of Human VEGF-A and P1GF Binding to Human VEGFR1 By Antibody II Measured by Solid Phase ELISA and Cell Based VEGFR1 Phosphorylation Assays The ability of VEGFR1 antibodies to bind to VEGFR1 and neutralize binding of VEGF-A and P1GF to VEGFR1 can be measured by solid phase ELISA and by cell-based VEGFR1 phosphorylation assays. VEGF-A and P1GF neutralization may be used in the analysis to demonstrate that the disclosed antibodies to mouse VEGFR1 function similarly in vitro to the disclosed antibodies to human VEGFR1.

For the solid phase ELISA, a 96-well plate may be coated with 1 μg/mL of hVEGFR1-Fc (R&D 321-fl 050/cf) in PBS at 50 μl/well, and then incubated overnight at 4° C. The solution may then be removed from the wells, and then the wells may be blocked for 1 hour with 100 μl of 1% casein at room temperature. Antibodies (including control Ron antibody (R&D MAB691)) may be titrated in a microtiter plate against PBSt (PBS containing Tween 20) starting at 50 μg/mL, and diluting with 1:3 dilutions to 0.023 μg/mL (see Table 4a). The ELISA plate may be washed 3 times with PBSt, and then 50 μl/well of pre-titrated antibody may be added. After a one hour incubation at 37° C., 50 μl of biotinylated ligand (2 nM hPLGF1 (Pepro Tech #AF-100 06) or 2 nM hVEGFA-165 (R&D #293-VE) may be added to each well, and incubation continued at 37° C. for 30 min. The plate may be washed 3 times with PBSt, and then 50 μl/well of NA-AP (1:1000 dilution) may be added, with an incubation at room temperature of 15 min. After washing three more times, 100 μl/well of PMP (1:35 diluted in water) may be added. The plate may then be developed for 30 min and read at $OD_{560}$.

For the cell-based VEGFR1 phosphorylation assay, PAE-R1 cells expressing human VEGFR1 may be seeded into 24-well tissue culture plates at 100,000 cells/well, and cultured overnight at 37° C. with 5% $CO_2$. The culture medium may then be changed to 500 μl of starvation medium (DMEM/F12 containing 0.1% BSA), and cultured overnight. Antibodies may then be added into the medium, and the cells cultured for 30 minutes. Human VEGF-A165 (R&D cat#293-VE) or human P1GF (R&D cat#264-PG) may then be added and the cells incubated for another 10 minutes. Phosphorylated human VEGFR1 may be determined using an ELISA (R&D Duo Set IC ELISA development kit, #DYC4170-2).

Data may be expressed as mean+/−standard error. JMP8 may be used for ANOVA analysis followed by Dunnett's comparison. $IC_{50}$ may be calculated using GraphPad Prism version 4. A P value less than 0.05 may be considered as statistically significant.

In experiments performed essentially as described above in this Example 4, Antibody II neutralizes human VEGF-A and P1GF binding to VEGFR1, and also suppresses human VEGF-A and P1GF stimulated VEGFR1 phosphorylation. Antibody II neutralizes P1GF and VEGF-A binding to VEGFR1 with an $IC_{50}$ of 0.43 nM and 0.14 nM, respectively (Table 4a).

Data points at low antibody concentrations are required to accurately calculate the $IC_{50}$. Accordingly, the experiment is repeated at antibody concentrations starting at 5 μg/mL and diluting with 1:3 dilutions to 0.0023 μg/mL. The experimental procedure may be as described below.

For the solid phase ELISA, a 96-well plate may be coated with 1 μg/mL of hVEGFR1-Fc (R&D 321-fl 050/cf) in PBS at 50 μl/well, and then incubated overnight at 4° C. The solution may then be removed from the wells, and then the wells may be blocked for 1 hour with 100 μl of 1% casein at room temperature. Antibodies (including control Ron antibody (R&D MAB691)) may be titrated in a microtiter plate against PBSt (PBS containing Tween 20) starting at 5 μg/mL, and diluting with 1:3 dilutions to 0.0023 μg/mL (see Table 4b). The ELISA plate may be washed 3 times with PBSt, and then 50 μl/well of pre-titrated antibody may be added. After a one hour incubation at 37° C., 50 μl of biotinylated ligand (4 nM hPLGF1 (R&D Cat#264-PG-010) or 2 nM hVEGFA-165 (R&D #293-VE) may be added to each well, and incubation continued at 37° C. for 30 min. The plate may be washed 3 times with PBSt, and then 50 μl/well of NA-AP (1:1000 dilution) may be added, with an incubation at room temperature of 15 min. After washing three more times, 100 μl/well of PMP (1:35 diluted in water) may be added. The plate may then be developed for 30 min and read at $OD_{560}$.

Data may be expressed as mean+/−standard error. JMP8 may be used for ANOVA analysis followed by Dunnett's comparison. $IC_{50}$ may be calculated using GraphPad Prism version 6. A P value less than 0.05 may be considered as statistically significant.

In the repeated experiments performed essentially as described above, Antibody II neutralizes human VEGF-A and P1GF binding to VEGFR1, and also suppresses human VEGF-A and P1GF stimulated VEGFR1 phosphorylation. Antibody II neutralizes P1GF and VEGF-A binding to VEGFR1 with an $IC_{50}$ of 0.31 nM and 1.02 nM, respectively (Table 4b).

Antibody II blocks both VEGF and PlGF stimulated VEGFR1 phosphorylation in vitro as seen in Table 5.

TABLE 4a

Neutralization of human VEGF-A and PlGF binding

| | Ab II (µg/ml) | | | | | | | |
|---|---|---|---|---|---|---|---|---|
| | 50.000 | 16.667 | 5.556 | 1.852 | 0.617 | 0.206 | 0.069 | 0.023 |
| Antibody II blocks human PlGF binding to VEGFR1 | | | | | | | | |
| OD-Ab II | 0.130 | 0.126 | 0.129 | 0.127 | 0.120 | 0.123 | 0.150 | 0.213 |
| Control Ab (µg/ml) | 50.000 | 16.667 | 5.556 | 1.852 | 0.617 | 0.206 | 0.069 | 0.023 |
| OD-Control mAb | 0.339 | 0.304 | 0.298 | 0.300 | 0.295 | 0.315 | 0.283 | 0.296 |
| Antibody II blocks human VEGF-A binding to VEGFR1 | | | | | | | | |
| OD-Ab II | 0.135 | 0.134 | 0.144 | 0.181 | 0.166 | 0.194 | 0.296 | 0.414 |
| Control Ab (µg/ml) | 50.000 | 16.667 | 5.556 | 1.852 | 0.617 | 0.206 | 0.069 | 0.023 |
| OD-Control Ab | 0.515 | 0.566 | 0.535 | 0.530 | 0.535 | 0.554 | 0.519 | 0.506 |

TABLE 4b

Neutralization of human VEGF-A and PlGF binding

| | Ab II (µg/ml) | | | | | | | |
|---|---|---|---|---|---|---|---|---|
| | 5.0000 | 1.6667 | 0.5556 | 0.1852 | 0.0617 | 0.0206 | 0.0069 | 0.0023 |
| Antibody II blocks human PlGF binding to VEGFR1 | | | | | | | | |
| OD-Ab II | 0.1366 | 0.1325 | 0.1350 | 0.1645 | 0.2346 | 0.3747 | 0.3955 | 0.4291 |
| Control Ab (µg/ml) | 5.0000 | 1.6667 | 0.5556 | 0.1852 | 0.0617 | 0.0206 | 0.0069 | 0.0023 |
| OD-Control mAb | 0.4068 | 0.4318 | 0.4363 | 0.4052 | 0.4076 | 0.3886 | 0.370 | 0.3593 |
| Antibody II blocks human VEGF-A binding to VEGFR1 | | | | | | | | |
| OD-Ab II | 0.3614 | 0.4569 | 0.5745 | 0.8829 | 1.2888 | 1.5889 | 1.4418 | 1.598 |
| Control Ab (µg/ml) | 5.0000 | 1.6667 | 0.5556 | 0.1852 | 0.0617 | 0.0206 | 0.0069 | 0.0023 |
| OD-Control Ab | 1.5116 | 1.4165 | 1.4701 | 1.4571 | 1.5133 | 1.6151 | 1.5255 | 1.5426 |

TABLE 5

Phosphorylation in cultured PAE-R1 cells expressing human VEGFR1

| | pVEGFR1 (OD) |
|---|---|
| SFM | 0.2590 +/− 0.0090 |
| Human IgG4 | 0.2390 +/− 0.0090 |
| Antibody II | 0.2445 +/− 0.0075 |
| VEGF-A | 0.5430 +/− 0.0270 |
| Antibody II + VEGF-A | 0.3150 +/− 0.0040 |
| PlGF | 0.5330 +/− 0.0240 |
| Antibody II + PlGF | 0.2735 +/− 0.0015 |

P < 0.001. Comparisons with a control (SFM) using Dunnett's Method.

EXAMPLE 5

Antibody II and IV Attenuate the Suppressing Effect of sFlt1 on VEGF-A Mediated ERK Phosphorylation The ability of VEGFR1 antibodies to attenuate the suppression of VEGF-A mediated ERK phosphorylation by sFlt1 can be measured in cultured hUVEC and bEnd3 cells. Suppression of VEGF-A mediated ERK phosphorylation may be used in the analysis to demonstrate that the disclosed antibodies to mouse VEGFR1 function similarly in vitro to the disclosed antibodies to human VEGFR1.

For measurement in bEnd3 cells, bEnd3 cells may be purchased from ATCC (#CRL-2299). The bEnd3 cells may be resuspended to $3\times10^5$ cells/mL in DMEM/high glucose medium (HyClone #SH30243.01) containing Anti/Anti (Thermo #SV30079.01) and 10% fetal bovine serum (Invitrogen #10082-147). 0.5 mL of resuspended bEnd.3 cells (containing approximately $1.5\times10^5$ cells) may be added to each well of a 24-well microtiter plates (Costar #3524) and incubated at 37° C., 5% $CO_2$, for 24 hrs. Medium may then be aspirated, and then cells may be starved in 500 µL/well of DMEM/high glucose medium containing Anti/Anti and 0.1% bovine serum albumin (BSA) (Sigma #A7979) at 37° C., 5% $CO_2$, for 15 hours. Before adding VEGF-A, sFlt1, and/or VEGFR1 antibody, the medium may be changed to fresh starvation medium with 0.1% BSA.

For VEGF-A treatment, 50 µL of 10× concentrations of mouse VEGF164 (8 ng/mL final) (R&D #493-MV/CF) may be added to each well and cells incubated for 10 min at 37° C., 5% $CO_2$. For VEGF-A plus sFlt1 treatment, 30 µL of 20× concentrations of mouse VEGF164 (8 ng/mL final) may be pre-mixed with 30 µL of mouse sFlt1 (40 ng/mL final, R&D #471-F1) for 30 min at 37° C., then the 50 µL of mixture may be added to each well and the cells incubated for 10 min at 37° C., 5% $CO_2$. For VEGF-A plus sFlt1 and Antibody IV, 20 µL of 30× concentrations of Antibody IV (500 ng/mL final) may be pre-mixed with mouse sFlt1 (40 ng/mL final, R&D 471-F1) for 30 min at 37° C. Next, 40 µL of 30× concentrations of mouse VEGF164 (8 ng/mL final) may be added to the mixture of Antibody IV and sFlt1. 50 µL of the final mixture may be added to each well and cells incubated for 10 min at 37° C., 5% $CO_2$. For the serum free medium control group, 50 µL of starvation medium with 0.1% BSA may be added to each well and cells incubated for 10 min at 37° C., 5% $CO_2$.

For measurement in hUVE cells, hUVE cells may be resuspended to $3\times10^5$ cells/mL in EGM-2 medium (Lonza # CC-3156) with supplements (Lonza # CC-4176). 0.5 mL of resuspended hUVE cells may be added to each well of 24-well microtiter plates (Costar #3524) ($1.5\times10^5$ cells/well) and incubated at 37° C., 5% $CO_2$, for 24 hours. The medium may then be changed to 500 µL/well EGM-2 medium containing 0.1% bovine serum albumin (BSA) (Sigma #A7979) for starvation for 15 hours at 37° C., 5% $CO_2$. Before adding treatment compound, the medium may be changed to fresh starvation medium with 0.1% BSA. For VEGF-A treatment, 50 µL of 10× concentrations of human VEGF165 (1.5 ng/mL final) (R&D 293-VE) may be added and cells incubated at 37° C., 5% $CO_2$, for 10 min. For VEGF-A plus sFlt1, 30 µL of 20× concentrations of human VEGF165 (1.5 ng/mL final) may be mixed with human sFlt1 (40 ng/mL final, R&D 321-FL/CF) at 37° C. for 30 min. 50 µL of the mixture may then be added to the well and cells incubated at 37° C., 5% $CO_2$, for 10 min. For VEGF-A plus sFlt1 and Antibody II, 20 µL of 30× concentrations of Antibody II (73 µL/mL final) may be pre-mixed with human sFlt1 (40 ng/mL final) for 30 min at 37° C., and 40 µL of 30× concentrations of human VEGF165 (1.5 ng/mL final) may then be added to the mixture of VEGF-A and sFlt1. 50 µL of the final mixture may be added to the well and cells incubated at 37° C., 5% $CO_2$, for 10 min. For the serum free medium control group, 50 µL of starvation medium with 0.1% BSA may be added to each well and cells incubated at 37° C., 5% $CO_2$, for 10 min.

For cell lysate preparation, 10 mL of Tris Lysis buffer (MSD) may be mixed with 200 µL protease inhibitor solution (50× stock), 100 µL phosphatase inhibitor I (100× stock), 100 µL phosphatase inhibitor II (100× stock), 40 µL phenylmethanesulfonylfuoride (PMSF) in DMSO (250× stock), and 100 µL SDS (10% stock). PMSF and SDS may be added immediately before using. After removing treatment medium, 50 µL of cell lysis buffer may be added to each well. The cells may be incubated with lysis buffer on ice for 10 min and then shaken at 4° C. for 30 min. The protein concentration of the lysate may be determined using Pierce BCA protein assay kit, cat#23227.

For the ERK1/2 phosphorylation assay, phosphorylated ERK1/2 may be determined following the protocol of a sandwich immunoassay developed by MSD (Phospho-ERK1/2 (Thr202/Tyr204; Thr185/Tyr187) Assay Whole Cell Lysate Kit; MSD #K151DWD-1). The assay may use a plate pre-coated with capture antibody for phosphorylated ERK1/2 (Thr202/Tyr204; Thr185/Tyr187). After adding samples, a solution containing the detection antibody, anti-total ERK1/2 conjugated with an electrochemiluminescent compound (MSD SULFO-TAG label), may be added. The MSD SECTOR Imager may be used for measuring intensity of emitted light correlated with phosphorylated ERK1/2 level in the sample. Both capture and detection antibodies cross react with human and mouse whole cell lysates.

Data may be expressed as mean+/−standard error. JMP8 may be used for ANOVA analysis followed by Dunnett's comparison.

In experiments performed essentially as described in this Example 5, Antibody II and Antibody IV attenuate sFlt1 activity in cultured hUVEC and bEnd3 cells, respectively (Table 6). Pre-incubation of sFlt1 with Antibody IV before mixing with mouse VEGF-A164 significantly prevents sFlt1's suppressive effect on VEGF-A stimulated ERK1/2 phosphorylation in bEnd3 cells. Final concentration of Antibody IV is 500 ng/mL in the study. Similar to Antibody IV, pre-incubation of sFlt with Antibody II before mixing with human VEGF-A165 significantly decreases VEGF-A165 stimulated ERK1/2 phosphorylation in hUVE cells. Final concentration of Antibody II is 73 µg/mL in the study. These results demonstrate that both Antibody II and IV block the Flt1 trapping of VEGF-A, which may result in increased accessibility of VEGF-A to VEGFR2.

TABLE 6

Antibody II and IV attenuate sFlt1 activity in bEnd3 and hUVE cells

| | pERK1/2 (OD) |
|---|---|
| hUVEC | |
| Control | 2940.5 +/− 358.5 |
| hVEGF-A | 24418.0 +/− 2300.0* |
| hVEGF-A + sFlt1 | 10532.5 +/− 3080.5 |
| hVEGFA + sFlt1 + Antibody II | 20877.5 +/− 1354.5* |
| bEnd3 | |
| Control | 2907.0 +/− 426.5 |
| mVEGF-A | 17106.5 +/− 1185.5** |
| mVEGF-A + sFlt1 | 3064.0 +/− 42.0 |
| mVEGFA + sFlt1 + Antibody IV | 16438.5 +/− 346.5** |

*$p < 0.01$,
**$p < 0.001$.
Comparisons with a control (SFM) using Dunnett's Method.

EXAMPLE 6

Antibody III and IV Decreases Albuminuria and Improves Renal Histopathological Lesions in Remnant Kidney Mouse Model The potential for VEGFR1 antibodies to improve albuminuria and renal histopathological lesions, both indicators of CKD, can be measured in vivo in a remnant kidney mouse model (Leelahavanichkul, et al. (2010) Kidney Int. 78(11): 1136-1153).

The remnant kidney model may be generated by surgically remove three-quarters of the mouse kidney mass at approximately 8 weeks of age. The model resembles human chronic kidney disease (CKD) developing albuminuria, hypertension, and renal lesions including mesangial expansion, glomerulosclerosis, and interstitial fibrosis. Remnant kidney surgery may be conducted in 129S6/SvEvTac male mice at 8-9 weeks of age. A modified one stage procedure for three-quarters reduction of total renal mass may be used where two poles of one kidney may be excised using cauterization, followed by a nephrectomy of the second kidney. Surgical staples may be removed one week post surgery. Mice may be housed individually on High Density racks in micro-isolator caging, sawdust bedding nestles for enrichment, in a room maintained at 75° F. on a 12 hour light/dark cycle and humidity 50%. Mice may have free access to bottle water and Purina 5008 diet. House water may be tap water filtered through reverse osmosis and chlorinated, with pH 6.5-7. The remnant kidney mice may be randomized by baseline urinary ACR and body weight 2 weeks post surgery.

For urine collection and urinary albumin and creatinine measurement, spot urine may be collected by placing a single animal on a 96 well Corning #3359 polypropylene microtiter plate. A plexiglas housing chamber may be secured over the mouse and plate. The urine may be transferred into a 1.5 mL Eppendorf tube on ice using a micropipette, and centrifuged at 10,000 rpm for 5 minutes. Urinary albumin may be measured using an internally validated assay and urinary creatinine may be measured using an enzymatic method.

For renal pathology, kidneys may be collected at the end of studies, fixed in formalin, and processed for paraffin sectioning according to standard methodology. Sections of kidney may be evaluated for renal lesions by a pathologist. Mesangial matrix, glomerular fibrosis, and interstitial fibrosis, may be semi-quantitatively scored using the following scale: none (0), minimal (1), slight (2), moderate (3), marked (4) and severe (5). Glomerular mesangial matrix expansion and basement membrane thickening may be scored using H&E and PAS stained sections. Masson's trichrome stained sections of kidney may be evaluated to determine the degree of fibrosis (interstitial and glomerular).

For measurement of systolic blood pressure, blood pressure may be measured using tail cuff method (Coda System, Kent Scientific) where mice may be acclimated to the restraint by placing them in the mouse holder with tail cuff attached for 5 minutes daily, 3-5 days prior to the actual measurement. The equipment room temperature may be increased to 75° F. to provide additional warmth during the blood pressure collection process. Mice may be selected and randomized. The mice may be placed in a holder/restrainer and set on top of the Coda warming pad unit (31-33° C.). The tail may be placed through the tail cuffs and each mouse may be restrained for approximately 30 minutes. The tail cuff may be inflated, compressing the tail tightly enough to momentarily interrupt arterial blood flow, and then gradually loosened by deflation to observe the return of the arterial pulse. On return of arterial pulse, the cuff may be fully deflated. Average of repeat measurements from one mouse may be used as level of systolic blood pressure for that mouse.

Data may be presented as mean+/−SE. GraphPad Prism or JMP may be used for ANOVA or unpaired t-test analysis. For analysis, urinary ACR data may be transformed to logarithm values. Graphpad Prism or JMP may be used for ANOVA analysis followed by Dunnett's multiple comparison test. A P value less than 0.05 may be considered statistically significant.

In experiments performed essentially as described in this Example 6, three studies are performed. For Study 1, six groups are included: (1) PBS, three time a week (tiw), n=12; (2) mouse IgG1 at 10 mg/kg, tiw, n=12; (3) Antibody IV at 10 mg/kg, tiw, n=12; (4) Antibody IV at 3 mg/kg, tiw, n=12; (5) Antibody IV at 3 mg/kg, qw, n=12; and (6) Antibody IV at 1 mg/kg, tiw, n=12. 0.2 mL of testing or control compounds is injected subcutaneously (sc) at the doses and intervals indicated above for sixteen weeks. Spot urine and body weight are collected at baseline (before treatment) and again at weeks 3, 6, 10, 12 and 16 of dosing. Systolic blood pressures are collected at week 16 of dosing. Samples collected at the end of the eight weeks of study include EDTA-anticoagulated whole blood and kidneys. EDTA plasma is used to measure BUN, creatinine, and other parameters. One half of the coronally sectioned remnant kidney is fixed in 10% nBF (neutral buffered formalin) for histopathological examination, the other half of remnant kidney is flash frozen in −80° C. for future analysis.

For Study 2, five groups are included in this study: (1) sham control (n=4, without treatment); (2) PBS control (n=10); (3) rat IgG1 at 10 mg/kg (n=10); (4) Antibody III at 10 mg/kg, (n=10); and (5) Antibody III at 3 mg/kg (n=10). All groups are dosed three times (tiw) a week intraperitoneally (i.p.) at a volume of 0.2 mL/mouse, for eight weeks. Spot urine is collected and body weight measured at randomization (baseline) and again at weeks 4, 6 and 8 of dosing. Systolic blood pressures are collected at weeks 4, and 8 of dosing. Blood pressure is determined using tail cuff. Endpoint samples collection is the same as described in Study 1.

For Study 3, nine groups are included: (1) sham operation group, no treatment, n=4; (2) PBS control, tiw, n=6; (3) rat IgG1 at 30 mg/kg, biw, n=10; (4) Antibody III at 30 mg/kg, biw, n=10; (5) Antibody III at 10 mg/kg, tiw, n=10; (6) Antibody III at 10 mg/kg, qw, n=10; (7) Antibody III at 3 mg/kg, tiw, n=10; (8) Antibody III at 3 mg/kg, qw, n=10; and (9) Antibody III at 1 mg/kg, qw, n=10. Compounds are injected subcutaneously (sc) at a volume of 0.2 mL/mouse for six weeks. Spot urine and body weight are collected at baseline (before treatment) and at weeks 2, 4 and 6 of dosing. Systolic blood pressures are collected at week 6 of dosing using tail cuff method. Endpoint sample collection is the same as described in Study 1.

Studies 1, 2, and 3 demonstrate that Antibody III (3 and 10 mg/kg) and Antibody IV (1, 3, and 10 mg/kg) significantly decrease albuminuria in comparison to the control at the corresponding time point, as measured by urinary albumin/creatinine (ACR), in remnant kidney mice (Tables 7-9). Antibody III and Antibody IV at the 10 mg/kg, 30 mg/kg, and 3 mg/kg (tiw) dosing groups also improve renal histopathological scores, as measured by renal glomerular fibrosis, interstitial fibrosis, and Masson's scores, in remnant kidney mice (Tables 10-11).

TABLE 7

Antibody IV decreases ACR in remnant kidney mice (Study 1)

| Group | Baseline (µg/mg) | Week 3 (µg/mg) | Week 6 (µg/mg) | Week 10 (µg/mg) | Week 16 (µg/mg) |
| --- | --- | --- | --- | --- | --- |
| PBS Control | 1255.5 +/− 584.2 | 2008.6 +/− 655.5 | 3363.0 +/− 1396.7 | 3090.1 +/− 1060.3 | 3926.3 +/− 1780.4 |
| mIgG1 10 mg/kg tiw | 1051.5 +/− 501.0 | 1780.0 +/− 571.6 | 2628.3 +/− 795.3 | 3559.3 +/− 1414.3 | 2269.3 +/− 646.1 |
| Antibody IV 10 mg/kg tiw | 1069.9 +/− 369.0 | 674.9 +/− 355.4 | 125.5 +/− 37.6 | 253.7 +/− 71.5 | 231.2 +/− 111.2 |
| Antibody IV 3 mg/kg tiw | 992.5 +/− 308.8 | 410.1 +/− 259.3 | 509.5 +/− 170.2 | 780.7 +/− 224.1 | 538.3 +/− 165.7 |
| Antibody IV 3 mg/kg qw | 923.9 +/− 241.1 | 1654.1 +/− 654.5 | 1804.3 +/− 612.1 | 2107.4 +/− 619.7 | 1591.3 +/− 488.3 |
| Antibody IV 1 mg/kg tiw | 1015.7 +/− 331.9 | 577.0 +/− 151.8 | 947.0 +/− 154.1 | 1188.0 +/− 284.2 | 926.9 +/− 218.8 |

Data presented as mean +/− SE

TABLE 8

Antibody III decreases ACR in remnant kidney mice (Study 2)

| Group | n | baseline (µg/mg) | week 4 (µg/mg) | week 6 (µg/mg) | week 8 (µg/mg) |
|---|---|---|---|---|---|
| Sham Control | 4 | 19.2 +/- 4.4 | 12.5 +/- 1.2 | 12.1 +/- 2.0 | 9.0 +/- 1.0 |
| PBS Control | 10 | 1423.0 +/- 511.3 | 3406.6 +/- 861.5 | 2966.1 +/- 1136.5 | 2426.7 +/- 872.6 |
| rIgG1 10 mg/kg, tiw | 10 | 1293.0 +/- 408.5 | 5780.9 +/- 2170.2 | 5390.9 +/- 2387.3 | 6771.5 +/- 3277.7 |
| Antibody III 10 mg/kg, tiw | 10 | 1529.4 +/- 808.7 | 138.3 +/- 61.4 | 53.9 +/- 21.4 | 80.5 +/- 35.5 |
| Antibody III 3 mg/kg, tiw | 10 | 1792.7 +/- 772.5 | 937.3 +/- 507.5 | 2249.8 +/- 1501.5 | 2054.8 +/- 1024.8 |

Data presented as mean +/- SE

TABLE 9

Antibody III decreases ACR in remnant kidney mice (Study 3)

| Group | n | Baseline (µg/mg) | week 2 (µg/mg) | week 4 (µg/mg) | week 6 (µg/mg) |
|---|---|---|---|---|---|
| Sham | 4 | 19.5 +/- 2.7 | 14.2 +/- 0.5 | 11.1 +/- 1.1 | 11.8 +/- 2.6 |
| Saline | 6 | 1650.7 +/- 1047.1 | 1007.5 +/- 242.0 | 1502.5 +/- 335.0 | 1724.1 +/- 66.7 |
| rIgG1 30 mg/kg biw | 10 | 1444.3 +/- 358.6 | 1940.8 +/- 374.0 | 2594.3 +/- 617.3 | 2855.6 +/- 565.0 |
| Ab III 30 mg/kg biw | 10 | 1644.7 +/- 318.0 | 642.1 +/- 141.1 | 217.7 +/- 81.8 | 164.4 +/- 72.0 |
| Ab III 10 mg/kg tiw | 10 | 2246.3 +/- 657.1 | 1066.0 +/- 301.5 | 337.8 +/- 99.0 | 649.0 +/- 299.6 |
| Ab III 10 mg/kg qw | 10 | 1663.0 +/- 336.2 | 1002.1 +/- 194.4 | 593.7 +/- 223.1 | 1380.5 +/- 536.5 |
| Ab III 3 mg/kg tiw | 10 | 1833.9 +/- 496.9 | 717.1 +/- 180.9 | 250.9 +/- 71.6 | 555.2 +/- 106.9 |
| Ab III 3 mg/kg qw | 10 | 1741.6 +/- 605.7 | 1223.4 +/- 270.5 | 1617.1 +/- 205.7 | 3023.9 +/- 426.5 |
| Ab III 1 mg/kg qw | 10 | 1938.7 +/- 464.3 | 1880.2 +/- 651.0 | 2561.8 +/- 827.9 | 4085.9 +/- 1249.1 |

Data presented as mean +/- SE

TABLE 10

Renal histopathological scores in remnant kidney mice (Study 2)

| Group | Glomerular fibrosis score | Interstitial fibrosis score | Systolic BP (mmHg) |
|---|---|---|---|
| mIgG1 10 mg/kg tiw | 0.8 +/- 0.3 | 1.3 +/- 0.3 | 170 +/- 1.4 |
| Ab III 10 mg/kg tiw | 0.0 +/- 0.0 | 0.3 +/- 0.1 | 145 +/- 2.2 |

TABLE 11

Renal histopathological scores in remnant kidney mice (Study 3)

| Group | n | Interstitial fibrosis score | Masson's score | Glomerular fibrosis score |
|---|---|---|---|---|
| Sham | 4 | 0 | 0 | 0 |
| Saline | 6 | 1.17 +/- 0.17 | 1.17 +/- 0.17 | 0.50 +/- 0.22 |
| rIgG1 30 mg/kg biw | 10 | 1.50 +/- 0.27 | 1.30 +/- 0.15 | 0.30 +/- 0.15 |
| Ab III 30 mg/kg biw | 10 | 0.30 +/- 0.15 | 0.30 +/- 0.15 | 0 |
| Ab III 10 mg/kg tiw | 10 | 0.50 +/- 0.17 | 0.50 +/- 0.17 | 0 |
| Ab III 10 mg/kg qw | 10 | 0.40 +/- 0.22 | 0.40 +/- 0.22 | 0.30 +/- 0.15 |
| Ab III 3 mg/kg tiw | 10 | 0.30 +/- 0.15 | 0.30 +/- 0.15 | 0.10 +/- 0.10 |
| Ab III 3 mg/kg qw | 10 | 1.20 +/- 0.33 | 1.20 +/- 0.33 | 0.50 +/- 0.17 |
| Ab III 1 mg/kg qw | 10 | 1.20 +/- 0.25 | 1.20 +/- 0.25 | 0.20 +/- 0.13 |

EXAMPLE 7

Antibody III Decreases Albuminuria and Improves Renal Histological Lesions in Diabetic db/db and Uninephrectomized db/db Mice The potential for VEGFR1 antibodies to improve albuminuria and renal histological lesions, both indicators of CKD, can be measured in vivo in diabetic db/db and uninephrectomized db/db mice. db/db mice represent a type 2 diabetic mouse model developing albuminuria and renal histopathological lesions resembling human diabetic nephropathy (Sharma et al. (2003) *Am J Physiol Renal Physiol* 284: F1138). Uninephrectomized db/db mice develop more albuminuria and severe renal structural lesions than db/db mice without uninephrectomy (Ninichuk et al. (2007) Eur J Med Res 12:351).

For urine collection and urinary albumin and creatinine measurement, spot urine may be collected by placing a single animal on a 96 well Corning #3359 polypropylene microtiter plate. A plexiglas housing chamber may be secured over the mouse and plate. The urine may be transferred into a 1.5 mL Eppendorf tube on ice using a micropipette, and centrifuged at 10,000 rpm for 5 minutes. Urinary albumin may be measured using an internally validated assay and urinary creatinine may be measured using an enzymatic method.

For renal pathology, kidneys may be collected at the end of studies, fixed in formalin, and processed for paraffin sectioning according to standard methodology. Sections of kidney may be evaluated for renal lesions by a pathologist. Mesangial matrix, glomerular fibrosis, and interstitial fibrosis, may be semi-quantitatively scored using the following scale: none (0), minimal (1), slight (2), moderate (3), marked (4) and severe (5). Glomerular mesangial matrix expansion and basement membrane thickening may be scored using H&E and PAS stained sections. Masson's trichrome stained sections of kidney may be evaluated to determine the degree of fibrosis (interstitial and glomerular).

Data may be presented as mean+/−SE. GraphPad Prism or JMP may be used for ANOVA analysis followed by Dunnett's multiple comparison test. A P value less than 0.05 may be considered statistically significant.

In experiments performed essentially as described in this Example 7, two studies are performed. In Study 4, male db/db male mice (BKS.Cg-+Lepr$^{db}$/+Lepr$^{db}$/OlaHsd) are purchased from Harlan Laboratories (Indianapolis, Ind.), and randomized at seven weeks of age to receive PBS, control rat IgG1 at 10 mg/kg, Antibody III at 10 mg/kg, and Antibody III at 3 mg/kg, respectively, three time per week (tiw) for six weeks. Mouse number in each group is ten except for PBS group with eight mice. Albumin/creatinine (ACR) is determined in spot urine collected at week 4 and 6 of treatment. Blood parameters and kidney histology are examined at the end of the six week study.

In Study 5, uninephrectomy surgery is conducted in db/db mice (BKS.Cg-+Lepr db/+Lepr db/OlaHsd) at 4 weeks of age, according to IACUC and their institutional guidelines. The mice are randomized at approximately 8-9 weeks of age. Seven groups are included in the study: (1) PBS control, n=6; (2) rat IgG1 at 30 mg/kg, biw, n=10; (3) Antibody III at 30 mg/kg, biw, n=10; (4) Antibody III at 10 mg/kg, tiw, n=10; (5) Antibody III at 10 mg/kg, qw, n=10; (6) Antibody III at 3 mg/kg, qw, n=10; and (7) Antibody III at 1 mg/kg, qw, n=10. Animals are dosed at 0.2 mL/injection, subcutaneously (sc), for six weeks. Blood glucose, body weight, spot urine ACR are examined periodically as indicated in Tables 13 and 15. Blood creatinine, BUN, and renal histology are examined at the end of the six week study.

In Studies 4 and 5, Antibody III significantly decreased urinary albumin/creatinine (ACR) in comparison to the control antibody for both 10 mg/kg, tiw, and 3 mg/kg, tiw, doses in db/db mice, and for all tested doses (30 mg/kg, tiw; 10 mg/kg, tiw; 10 mg/kg, qw; 3 mg/kg, tiw; 3 mg/kg, qw, and 1 mg/kg, qw) in uninephrectomized db/db mice (Tables 12-13). Antibody III also improves renal histopathological scores, as measured by Mesangial Matrix Scores, and decreases blood urea nitrogen (BUN) in uninephrectomized db/db mice (Table 14 and 15).

TABLE 12

Antibody III decreases ACR in db/db mice (Study 4)

| Group | n | Baseline (µg/mg) | Week 4 (µg/mg) | Week 6 (µg/mg) |
|---|---|---|---|---|
| PBS | 8 | 273.3 +/− 61.5 | 438.8 +/− 64.6 | 520.3 +/− 64.5 |
| ratIgG1 10 mg/kg, tiw | 10 | 281.3 +/− 49.9 | 540.8 +/− 61.4 | 519.1 +/− 66.6 |
| Antibody III 10 mg/kg, tiw | 10 | 279.5 +/− 53.1 | 172.2 +/− 39.2 | 110.9 +/− 12.2 |
| Antibody III 3 mg/kg, tiw | 10 | 287.4 +/− 52.6 | 265.4 +/− 57.3 | 150.1 +/− 24.0 |

TABLE 13

Antibody III decreases ACR in uninephrectomized db/db mice (Study 5)

| Group | n | Baseline (µg/mg) | Week 2 (µg/mg) | Week 4 (µg/mg) | Week 6 (µg/mg) |
|---|---|---|---|---|---|
| Saline | 6 | 477.9 +/− 166.4 | 622.5 +/− 108.8 | 1577.3 +/− 430.9 | 2199.5 +/− 327.4 |
| Rat IgG 30 mg/kg biw | 10 | 459.7 +/− 103.4 | 1430.3 +/− 261.4 | 2501.9 +/− 284.2 | 2461.4 +/− 235.4 |
| Antibody III 30 mg/kg biw | 10 | 471.5 +/− 94.7 | 576.1 +/− 217.9 | 467.0 +/− 88.5 | 468.3 +/− 155.8 |
| Antibody III 10 mg/kg tiw | 10 | 445.0 +/− 78.9 | 609.2 +/− 110.6 | 631.2 +/− 132.9 | 646.0 +/− 123.9 |
| Antibody III 10 mg/kg qw | 10 | 467.0 +/− 128.9 | 669.9 +/− 150.9 | 1377.6 +/− 386.1 | 726.1 +/− 91.7 |
| Antibody III 3 mg/kg tiw | 10 | 433.9 +/− 148.1 | 1028.6 +/− 377.2 | 1308.7 +/− 246.9 | 1759.1 +/− 340.8 |
| Antibody III 1 mg/kg qw | 10 | 387.2 +/− 73.8 | 511.8 +/− 101.5 | 1367.9 +/− 247.5 | 1700.6 +/− 239.7 |

TABLE 14

Antibody III improves renal histological lesions in uninephrectomized db/db mice

| | Animal number (n) | Mesangial Matrix Scores |
|---|---|---|
| Saline | 6 | 1.8 +/− 0.2 |
| Rat IgG1-30 mg/kg biw | 10 | 1.7 +/− 0.2 |
| Antibody III - 30 mg/kg biw | 10 | 1.1 +/− 0.1 |
| Antibody III -10 mg/kg tiw | 10 | 1.4 +/− 0.2 |
| Antibody III -10 mg/kg qw | 10 | 1.1 +/− 0.1 |
| Antibody III -3 mg/kg qw | 10 | 1.1 +/− 0.1 |
| Antibody III -1 mg/kg qw | 10 | 1.0 |

TABLE 15

Effect of Antibody III on body weight, glucose, cholesterol, BUN, and FFA on uninephrectomized db/db mice

| | Saline | Rat IgG1 30 mg/kg biw | Ab III 30 mg/kg biw | Ab III 10 mg/kg tiw | Ab III 10 mg/kg qw | Ab III 3 mg/kg qw | Ab III 1 mg/kg qw |
|---|---|---|---|---|---|---|---|
| Body weight (g) | 56.1 +/− 1.6 | 54.4 +/− 2.9 | 58.4 +/− 1.0 | 52.8 +/− 0.8 | 57.4 +/− 0.6 | 56.4 +/− 0.6 | 56.4 +/− 0.8 |
| Blood glucose (mg/dL) | 551.2 +/− 23.5 | 581.6 +/− 9.9 | 585.1 +/− 9.5 | 588.5 +/− 10.9 | 601 +/− 0.0 | 548.2 +/− 19.2 | 535.4 +/− 24.4 |

TABLE 15-continued

Effect of Antibody III on body weight, glucose, cholesterol, BUN, and FFA on uninephrectomized db/db mice

|  | Saline | Rat IgG1 30 mg/kg biw | Ab III 30 mg/kg biw | Ab III 10 mg/kg tiw | Ab III 10 mg/kg qw | Ab III 3 mg/kg qw | Ab III 1 mg/kg qw |
|---|---|---|---|---|---|---|---|
| Plasma BUN (mg/dL) | 37.9 +/− 1.1 | 40.2 +/− 1.6 | 33.2 +/− 1.1 | 30.2 +/− 1.5 | 31.3 +/− 1.3 | 35.2 +/− 1.0 | 33.1 +/− 1.0 |
| Cholesterol (mg/dL) | 221.8 +/− 5.4 | 227.9 +/− 9.3 | 194.5 +/− 5.3 | 199.9 +/− 9.4 | 195.1 +/− 7.4 | 216.6 +/− 11.8 | 231.5 +/− 7.7 |
| FFA (mmol/dL) | 2.5 +/− 0.4 | 2.8 +/− 0.3 | 2.0 +/− 0.1 | 1.9 +/− 0.1 | 2.0 +/− 0.1 | 2.1 +/− 0.1 | 2.6 +/− 0.2 |

EXAMPLE 8

Antibody IV Decreases Albuminuria, Prevents Serum Creatinine Increase, and Decreases Mortality in Diabetic db/db-eNOS Deficient Mice The potential for VEGFR1 antibodies to improve albuminuria and renal function, both indicators of CKD, can be measured in vivo in diabetic db/db-eNOS deficient mice. db/db-eNOS knockout mice represent a diabetic kidney injury model resembling a more advanced stage human diabetic nephropathy. The mice develop hyperglycemia, albuminuria, arteriolar hyalinosis, GBM thickness, mesangial expansion, mesangiolysis, focal segmental and early nodular glomerulosclerosis, as well as decline of glomerular filtration rate (GFR) (Zhao et al. (2006) J Am Soc Nephrol 17:2664). Without treatment, the mice exhibit high mortality after 16-20 weeks of age.

For urine collection and urinary albumin and creatinine measurement, spot urine may be collected by placing a single animal on a 96 well Corning #3359 polypropylene microtiter plate. A plexiglas housing chamber may be secured over the mouse and plate. The urine may be transferred into a 1.5 mL Eppendorf tube on ice using a micropipette, and centrifuged at 10,000 rpm for 5 minutes. Urinary albumin may be measured using an internally validated assay and urinary creatinine may be measured using an enzymatic method.

In experiments performed essentially as described in this Example 8, two studies examining Antibody IV efficacy are conducted in the diabetic db/db-eNOS knocking-out mice (Study 6 and Study 7).

For Study 6, the db/db-eNOS knock-out mice (BKS.Cg-Lepr<db>-Nos3<tm1Unc/Rhrs>) at 8 to 22 weeks of age are randomized into two groups: control group consisting of 6 male and five female mice receiving 10 mg/kg of mouse IgG1 and treatment group consisting of 6 male and 4 female mice receiving 10 mg/kg of Antibody IV. The antibodies are administrated three times a week (tiw), subcutaneously (sc), at a volume of 0.2 mL/injection, for 12 weeks. Serum creatinine is measured at the end of the study.

For Study 7, the db/db-eNOS knock-out mice are randomized into three groups to receive PBS, control mouse IgG1 at 10 mg/kg, and Antibody IV at 10 mg/kg, respectively. The PBS group consists of 11 mice including 5 male and 6 female mice. The Control IgG1 group consists of 11 mice including 6 male and 5 female mice. The Antibody IV group consists of 7 male and 5 female mice at the beginning of treatment. The Antibody IV and control reagents are administered three times a week (tiw), sc, for 12 weeks. Spot urine ACR levels are measured at baseline and week 2, 4, 6, 6, 10, and 12 of treatment. Serum creatinine is examined at baseline, and week 6 and week 12 of treatment.

Antibody IV significantly decreases albuminuria, as measured by urinary albumin/creatinine (ACR) in comparison to the control at the corresponding time point, in db/db-eNOS knockout mice (Table 16). Antibody IV also improved renal function, as measured by prevention of serum creatinine increase in diabetic db/db-eNOS knockout mice (Table 16). Among mice that survived to endpoint of the study, 69% in control group (PBS+IgG1, n=13) increased serum creatinine greater than 50% versus 10% in Antibody IV group (n=10; P=0.016 in chi-square test). Furthermore, 30% of mice in control group doubled serum creatinine while no mouse did in Antibody IV group. Antibody IV treatment decreases mortality in db/db-eNOS knock-out mice (Table 17).

TABLE 16

Antibody IV decreases ACR in diabetic db/db-eNOS deficient mice

| Group | Week 0 baseline (μg/mg) | Week 2 (μg/mg) | Week 4 (μg/mg) | Week 6 (μg/mg) |
|---|---|---|---|---|
| PBS | 11502.6 +/− 1451.1 | 33350.3 +/− 2880.5 | 51168.3 +/− 7966.4 | 58561.6 +/− 9937.8 |
| Control IgG1 10 mg/kg, tiw | 13186.0 +/− 2112.4 | 31400.7 +/− 4660.2 | 45277.1 +/− 6009.7 | 58445.8 +/− 5991.3 |
| Ab IV 10 mg/kg, tiw | 16972.3 +/− 2693.0 | 21815.3 +/− 4686.3 | 28199.8 +/− 7232.3 | 25653.3 +/− 7353.8 |

| Group | Week 8 (μg/mg) | Week 10 (μg/mg) | Week 12 (μg/mg) |
|---|---|---|---|
| PBS | 90540.6 +/− 19688.1 | 95784.9 +/− 17895.9 | 49514.8 +/− 8284.1 |
| Control IgG1 10 mg/kg, tiw | 63692.3 +/− 10104.8 | 92968.7 +/− 16816.8 | 137806.2 +/− 29612.0 |

TABLE 16-continued

Antibody IV decreases ACR in diabetic db/db-eNOS deficient mice

| Ab IV 10 mg/kg, tiw | 19753.9 +/− 4596.1 | 28873.2 +/− 9990.1 | 36793.8 +/− 14604.3 |

TABLE 17

Survival rate (%) in Antibody IV and control antibody treated diabetic db/db-eNOS knockout mice (Study 6 and 7)

|  | week 0 | week 4 | week 8 | week 10 | week 12 |
| --- | --- | --- | --- | --- | --- |
| control IgG1 10 mg/kg, tiw | 100 | 93.94 | 72.73 | 57.58 | 45.45 |
| Antibody IV 10 mg/kg, tiw | 100 | 90.91 | 86.36 | 81.82 | 81.82 |

EXAMPLE 9

Antibody II and III Effect on Blood P1GF Levels in Monkey and Mouse

The ability of VEGFR1 antibodies to affect in vivo blood P1GF levels can be measured in monkey and mouse. For measurement of P1GF in monkey plasma, a P1GF ELISA assay (R&D Systems #DPG00) may be used. For measurement of P1GF in mouse blood, a P1GF ELISA assay (R&D Systems, Quantikine Mouse P1GF-2 immunoassay; catalog # MP200) may be used. Serum and plasma samples may be diluted 2-20 fold into calibrator diluent (R&D Systems #RD5-17) prior to assay. Standard curve may range from 23.4 to 1500 pg/ml for mouse P1GF, and 15.6 to 1000 pg/ml for monkey P1GF. Data may be presented as mean+/−SE; and GraphPad Prism 4 may be used for data analysis.

In a Cynomolgus monkey study, the in vivo response of blood P1GF to Antibody II may be measured using plasma collected from four groups of monkeys (each group consisting of 4 male and 4 female monkeys) at 2.5-4.5 years of age. The monkeys may receive Antibody II at doses of 0, 3, 20, or 65 mg/kg, once a week (qw) for 13 weeks. The blood samples may be collected at the end of the study.

In a mouse study, the in vivo response of blood P1GF to Antibody III may be measured using blood collected from remnant mice or uninephrectomized db/db mice. In a remnant kidney mouse study, Antibody III may be dosed at 10 mg/kg and 3 mg/kg, three times a week (tiw), for eight weeks. In a uninephrectomized db/db study, Antibody III may be administrated at 30 mg/kg biw, 10 mg/kg tiw, 10 mg/kg qw, 3 mg/kg qw, and 1 mg/kg qw, for 6 weeks. Plasma samples may be collected at the end of the studies.

In experiments performed essentially as described in this Example 9, Antibody II significantly elevates plasma P1GF levels in cynomolgus monkeys at doses of 3, 20, and 65 mg/kg, once a week, for 13 weeks (Table 18). Antibody III dose dependently increases blood P1GF in both remnant kidney and uninephrectomized mice (Table 19). Table 18: Blood P1GF in Cynomolgus Monkey treated with Antibody II for 13 weeks

|  | Plasma P1GF (pg/mL) |
| --- | --- |
| Vehicle | 4.3 +/− 1.7 |
| Antibody II 3 mg/kg, qw | 527.6 +/− 94.9 |

-continued

|  | Plasma P1GF (pg/mL) |
| --- | --- |
| Antibody II 20 mg/kg, qw | 805.4 +/− 56.9 |
| Antibody II 65 mg/kg, qw | 807.5 +/− 129.4 |

$P < 0.01$ vs. Vehicle group

TABLE 19

Blood P1GF in mice treated with Antibody III

|  | Plasma P1GF (pg/ml) |
| --- | --- |
| Uninephrectomized db/db mouse study | |
| Saline | 12.6 +/− 4.8 |
| rIgG1-30 mg/kg, biw | 20.2 +/− 2.6 |
| Ab III-30 mg/kg, biw | 5849.3 +/− 530.4 |
| Ab III -10 mg/kg, tiw | 1605.1 +/− 201.7 |
| Ab III -10 mg/kg, qw | 520.8 +/− 117.3 |
| Ab III -3 mg/kg, qw | 20.1 +/− 2.4 |
| Ab III -1 mg/kg, qw | 21.6 +/− 1.8 |
| Remnant kidney mouse study | |
| PBS | 88.4 +/− 20.5 |
| rIgG1-10 mg/kg, tiw | 173.6 +/− 30.1 |
| Ab III -10 mg/kg, tiw | 5523.4 +/− 230.2 |
| Ab III -3 mg/kg, tiw | 1888.6 +/− 538.1 |

$P < 0.01$

EXAMPLE 10

Renal VEGFR2 Phosphorylation in Mouse and Monkey Kidneys

The ability of VEGFR1 antibodies to affect renal VEGFR2 phosphorylation can be measured in the kidneys of monkey and mouse.

Monkey kidneys may be collected from a Cynomolgus monkey study in which four groups of monkeys (each group consisting of 4 male and 4 female monkeys) at 2.5-4.5 years of age may be treated with Antibody II at doses of 0, 3, 20, and 65 mg/kg, respectively, once a week (qw), for 13 weeks. Monkeys in dose 0 group may receive a vehicle (PBS, pH7.4) injection. The kidney samples may be collected and frozen at the end of the study.

Monkey kidney homogenate may be prepared using QIAGEN TissueLyser where approximately 150 μg of monkey kidney tissue may be placed in a 2 ml QIAGEN tube on ice and then add 500 μL Sample Buffer (MSD phosphor-VEGFR2 cat# K151DJD-1). The tube may be shaken on a QIAGEN TissueLyser with stainless steel beads (5 mm, QIAGEN #69989) at 6.5 speeds for 60 seconds. The tube may be incubated on ice for 5 minutes followed by rotating tubes at 4° C. for 30 minutes. The tube may then be centrifuged at 4° C. and 8,000 rpm for 10 minutes. The supernatant may be removed to a fresh Eppendorf tube. Protein concentration in 1:100 diluted homogenate may be determined using BCA assay (Pierce BCA protein assay kit cat#23227). The sample may be stored at −80° C.

Phosphorylated VEGFR2 levels may be determined using the Phospho-VEGFR-2 (Tyr1054) assay whole cell lysate kit (MSD #K151DJD-1). Monkey kidney homogenate containing 400 µg total proteins may be loaded to each well.

Mouse kidneys may be collected from a remnant kidney study as described in Example 6, a uninephrectomized db/db mouse study as described in Example 7, or in normal 129 mice. In the 129 mouse study, male 129S6/SvEvTac mice from Taconic Farm may be randomized into two groups at approximately 10 weeks of age to receive either Antibody III or control rat IgG1 antibody. Both Antibody III and control IgG1 antibodies may be administered at 10 mg/kg, three times a week (tiw), sc, for 16 weeks. Kidneys may be collected at the end of the 16 week study.

Mouse kidney homogenate may be prepared by adding approximately 50 µg of mouse kidney to 300 µL of Sample Buffer (MSD mouse phospho-KDR (Tyr1175). Tube may be placed on ice and shaken on a FastPrep at 6.5 speed for 40 seconds. After 5 minutes of incubation on ice, tissues may be disrupted using the FastPrep. The tubes may be rotated at 4° C. for 30 minutes, followed by centrifuging at 4° C. and 8,000 rpm for 10 minutes. The supernatant may be removed to a fresh Eppendorf tube. The protein concentration in 1:100 diluted homogenate may be determined using the BCA method (Pierce BCA protein assay kit cat#23227). The sample may be stored at −80° C.

Phosphorylated mouse VEGFR2 may be determined using the Mouse phospho-KDR (Tyr1175) assay whole cell lysate kit (MSD custom#N45CA-1). Mouse kidney homogenate containing 400 µg total protein may be loaded to each well. OD may be read using the SECTOR Imager.

In experiments performed essentially as described in this Example 10, Antibody II increases renal VEGFR2 phosphorylation in Cynomolgus monkeys receiving 20 mg/kg, qw dose for 13 weeks (Table 20). Similarly, Antibody III increases renal VEGFR2 phosphorylation in remnant kidney mice receiving six weeks of Antibody III treatment (Table 21), in uninephrectomized db/db mice receiving six weeks of Antibody III treatment (Table 22), as well as in 129 mice receiving 16 weeks of Antibody III treatment (Table 23).

TABLE 20

VEGFR2 phosphorylation in monkey kidney after treatment with Antibody II

|  | pVEGFR2 (OD) |
| --- | --- |
| Vehicle | 93.38 +/− 8.702 |
| Antibody II | 177.88 +/− 25.423 |

$P < 0.05$

TABLE 21

Antibody III increases renal VEGFR2 phosphorylation in remnant mouse kidneys.

|  | pVEGFR2 (OD) +/− Standard Error | pVEGFR2 (OD) +/− Standard Median Error |
| --- | --- | --- |
| rIgG1-30 mg/kg biw |  | 513.00 +/− 26.985 |
| Antibody III -30 mg/kg biw |  | 848.25 +/− 78.996 |
| Antibody III -10 mg/kg qw | 657.25 +/− 535.24 | 657.25 +/− 65.984 |
| Antibody III -3 mg/kg qw | 464 +/− 341.99 | 464 +/− 34.945 |

$P < 0.003$ vs. rIgG1 control group, by ANOVA and Dunnett's comparison

TABLE 22

Antibody III increases VEGFR2 phosphorylation in uninephrectomized db/db mouse kidneys.

|  | pVEGFR2 (OD) +/− Standard Error | pVEGFR2 (OD) +/− Standard Median Error |
| --- | --- | --- |
| rIgG1 30 mg/kg, biw | 466.75 +/− 73.87 | 466.75 +/− 36.44 |
| Antibody III 30 mg/kg, biw | 1056.00 +/− 73.87 | 1056.00 +/− 110.94 |
| Antibody III 10 mg/kg, tiw | 590.50 +/− 60.32 | 590.50 +/− 49.84 |
| Antibody III 10 mg/kg, qw | 550.00 +/− 85.30 | 550.00 +/− 108.67 |
| Antibody III 3 mg/kg, qw | 373.00 +/− 73.87 | 373.00 +/− 57.91 |

$P < 0.0005$ vs. control IgG1 group, by ANOVA and Dunnett's comparison

TABLE 23

Antibody III increases renal VEGFR2 phosphorylation in 129S6/SvEvTac mouse kidneys

|  | pVEGFR2 (OD) |
| --- | --- |
| rIgG, 10 mg/kg tiw | 484.25 +/− 95.33 |
| Antibody III, 10 mg/kg tiw | 1039.00 +/− 60.29 |

$P < 0.001$ vs. control IgG1 group.

Amino Acid and Nucleotide Sequences

SEQ ID NO: 1
(hVEGFR1)
MVSYWDTGVLLCALLSCLLLTGSSSGSKLKDPELSLKGTQHIMQAGQTLH

LQCRGEAAHKWSLPEMVSKESERLSITKSACGRNGKQFCSTLTLNTAQAN

HTGFYSCKYLAVPTSKKKETESAIYIFISDTGRPFVEMYSEIPEIIHMTE

GRELVIPCRVTSPNITVTLKKFPLDTLIPDGKRIIWDSRKGFIISNATYK

EIGLLTCEATVNGHLYKTNYLTHRQTNTIIDVQISTPRPVKLLRGHTLVL

NCTATTPLNTRVQMTWSYPDEKNKRASVRRRIDQSNSHANIFYSVLTIDK

MQNKDKGLYTCRVRSGPSFKSVNTSVHIYDKAFITVKHRKQQVLETVAGK

RSYRLSMKVKAFPSPEVVWLKDGLPATEKSARYLTRGYSLIIKDVTEEDA

GNYTILLSIKQSNVFKNLTATLIVNVKPQIYEKAVSSFPDPALYPLGSRQ

ILTCTAYGIPQPTIKWFWHPCNHNHSEARCDFCSNNEESFILDADSNMGN

RIESITQRMAIIEGKNKMASTLVVADSRISGIYICIASNKVGTVGRNISF

YITDVPNGFHVNLEKMPTEGEDLKLSCTVNKFLYRDVTWILLRTVNNRTM

HYSISKQKMAITKEHSITLNLTIMNVSLQDSGTYACRARNVYTGEEILQK

KEITIRDQEAPYLLRNLSDHTVAISSSTTLDCHANGVPEPQITWFKNNHK

IQQEPGIILGPGSSTLFIERVTEEDEGVYHCKATNQKGSVESSAYLTVQG

TSDKSNLELITLTCTCVAAT LFWLLLTLFI

RKMKRSSSEIKTDYLSIIMDPDEVPLDEQCERLPYDASKWEFARERLKLG

KSLGRGAFGKVVQASAFGIKKSPTCRTVAVKMLKEGATASEYKALMTELK

ILTHIGHHLNVVNLLGACTKQGGPLMVIVEYCKYGNLSNYLKSKRDLFFL

NKDAALHMEPKKEKMEPGLEQGKKPRLDSVTSSESFASSGFQEDKSLSDV

EEEEDSDGFYKEPITMEDLISYSFQVARGMEFLSSRKCIHRDLAARNILL

SENNVVKICDFGLARDIYKNPDYVRKGDTRLPLKWMAPESIFDKIYSTKS

DVWSYGVLLWEIFSLGGSPYPGVQMDEDFCSRLREGMRMRAPEYSTPEIY

QIMLDCWHRDPKERPRFAELVEKLGDLLQANVQQDGKDYIPINAILTGNS

-continued

GFTYSTPAFSEDFFKESISAPKFNSGSSDDVRYVNAFKFMSLERIKTFEE

LLPNATSMFDDYQGDSSTLLASPMLKRFTWTDSKPKASLKIDLRVTSKSK

ESGLSDVSRPSFCHSSCGHVSEGKRRFTYDHAELERKIACCSPPPDYNSV

VLYSTPPI

SEQ ID NO: 2
(HCDR1 - Antibody 1 and 2)
GFAFSSYGMH

SEQ ID NO: 3
(HCDR2 - Antibody 1 and 2)
VIWYDGSNKYYADSVRG

SEQ ID NO: 4
(HCDR3 - Antibody 1 and 2)
DHYGSGVHHYFYYGLDV

SEQ ID NO: 5
(HCVR - Antibody 1 and 2)
QAQVVESGGGVVQSGRSLRLSCAASGFAFSSYGMHWVRQAPGKGLEWVAV

IWYDGSNKYYADSVRGRFTISRDNSENTLYLQMNSLRAEDTAVYYCARDH

YGSGVHHYFYYGLDVWGQGTTVTVSS

SEQ ID NO: 6
(HC - Antibody 1)
QAQVVESGGGVVQSGRSLRLSCAASGFAFSSYGMHWVRQAPGKGLEWVAV

IWYDGSNKYYADSVRGRFTISRDNSENTLYLQMNSLRAEDTAVYYCARDH

YGSGVHHYFYYGLDVWGQGTTVTVSSASTKGPSVFPLAPSSKSTSGGTAA

LGCLVKDYFPEPVTVSWNSGALTSGVHTFPAVLQSSGLYSLSSVVTVPSS

SLGTQTYICNVNHKPSNTKVDKRVEPKSCDKTHTCPPCPAPELLGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKG

QPREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKSL

SLSPGK

SEQ ID NO: 7
(HC - Antibody 2)
QAQVVESGGGVVQSGRSLRLSCAASGFAFSSYGMHWVRQAPGKGLEWVAV

IWYDGSNKYYADSVRGRFTISRDNSENTLYLQMNSLRAEDTAVYYCARDH

YGSGVHHYFYYGLDVWGQGTTVTVSSASTKGPSVFPLAPCSRSTSESTAA

LGCLVKDYFPEPVTVSWNSGALTSGVHTFPAVLQSSGLYSLSSVVTVPSS

SLGTKTYTCNVDHKPSNTKVDKRVESKYGPPCPPCPAPEAAGGPSVFLFP

PKPKDTLMISRTPEVTCVVVDVSQEDPEVQFNWYVDGVEVHNAKTKPREE

QFNSTYRVVSVLTVLHQDWLNGKEYKCKVSNKGLPSSIEKTISKAKGQPR

EPQVYTLPPSQEEMTKNQVSLTCLVKGFYPSDIAVEWESNGQPENNYKTT

PPVLDSDGSFFLYSRLTVDKSRWQEGNVFSCSVMHEALHNHYTQKSLSLS

LG

SEQ ID NO: 8
(LCDR1 - Antibody 1 and 2)
RASQSVSSSYLA

SEQ ID NO: 9
(LCDR2 - Antibody 1 and 2)
GASSRAT

SEQ ID NO: 10
(LCDR3 - Antibody 1 and 2)
QQYGSSPLT

SEQ ID NO: 11
(LCVR - Antibody 1 and 2)
EIVLTQSPGTLSLSPGERATLSCRASQSVSSSYLAWYQQKPGQAPRLLIY

GASSRATGIPDRFSGSGSGTDFTLTISRLEPEDFAVYYCQQYGSSPLTFG

GGTKVEIK

SEQ ID NO: 12
(LC - Antibody 1 and 2)
EIVLTQSPGTLSLSPGERATLSCRASQSVSSSYLAWYQQKPGQAPRLLIY

GASSRATGIPDRFSGSGSGTDFTLTISRLEPEDFAVYYCQQYGSSPLTFG

GGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

SEQ ID NO: 13
(HC DNA- Antibody 1)
CAGGCGCAGGTGGTGGAGTCTGGGGGAGGCGTGGTCCAGTCTGGGAGGTC

CCTGAGACTCTCCTGTGCAGCGTCTGGATTCGCCTTCAGTAGCTACGGCA

TGCACTGGGTCCGCCAGGCTCCAGGCAAGGGGCTGGAGTGGGTGGCAGTT

ATATGGTATGATGGAAGTAATAAATACTATGCAGACTCCGTGAGGGGCCG

ATTCACCATCTCCAGAGACAATTCCGAGAACACGCTGTATCTGCAAATGA

ACAGCCTGAGAGCCGAGGACACGGCTGTATATTACTGTGCGAGAGATCAC

TATGGTTCGGGGGTGCACCACTATTTCTACTACGGTCTGGACGTCTGGGG

CCAAGGGACCACGGTCACCGTCTCCTCAGCTAGCACCAAGGGCCCATCGG

TCTTCCCCCTGGCACCCTCCTCCAAGAGCACCTCTGGGGGCACAGCGGCC

CTGGGCTGCCTGGTCAAGGACTACTTCCCCGAACCGGTGACGGTGTCGTG

GAACTCAGGCGCCCTGACCAGCGGCGTGCACACCTTCCCGGCTGTCCTAC

AGTCCTCAGGACTCTACTCCCTCAGCAGCGTGGTGACCGTGCCCTCCAGC

AGCTTGGGCACCCAGACCTACATCTGCAACGTGAATCACAAGCCCAGCAA

CACCAAGGTGGACAAGAGAGTTGAGCCCAAATCTTGTGACAAAACTCACA

CATGCCCACCGTGCCCAGCACCTGAACTCCTGGGGGGACCGTCAGTCTTC

CTCTTCCCCCCAAAACCCAAGGACACCCTCATGATCTCCCGGACCCCTGA

GGTCACATGCGTGGTGGTGGACGTGAGCCACGAAGACCCTGAGGTCAAGT

TCAACTGGTATGTGGACGGCGTGGAGGTGCATAATGCCAAGACAAAGCCG

CGGGAGGAGCAGTACAACAGCACGTACCGTGTGGTCAGCGTCCTCACCGT

CCTGCACCAGGACTGGCTGAATGGCAAGGAGTACAAGTGCAAGGTCTCCA

ACAAAGCCCTCCCAGCCCCCATCGAGAAAACCATCTCCAAAGCCAAAGGG

CAGCCCCGAGAACCACAGGTGTACACCCTGCCCCCATCCCGGGAGGAGAT

GACCAAGAACCAGGTCAGCCTGACCTGCCTGGTCAAAGGCTTCTATCCCA

-continued
GCGACATCGCCGTGGAGTGGGAGAGCAATGGGCAGCCGGAGAACAACTAC
AAGACCACGCCTCCCGTGCTGGACTCCGACGGCTCCTTCTTCCTCTATAG
CAAGCTCACCGTGGACAAGAGCAGGTGGCAGCAGGGGAACGTCTTCTCAT
GCTCCGTGATGCATGAGGCTCTGCACAACCACTACACGCAGAAGAGCCTC
TCCCTGTCCCCGGGTAAA SEQ ID NO: 14
(HC DNA- Antibody 2)
CAGGCGCAGGTGGTGGAGTCTGGGGGAGGCGTGGTCCAGTCTGGGAGGTC
CCTGAGACTCTCCTGTGCAGCGTCTGGATTCGCCTTCAGTAGCTACGGCA
TGCACTGGGTCCGCCAGGCTCCAGGCAAGGGGCTGGAGTGGGTGGCAGTT
ATATGGTATGATGGAAGTAATAAATACTATGCAGACTCCGTGAGGGGCCG
ATTCACCATCTCCAGAGACAATTCCGAGAACACGCTGTATCTGCAAATGA
ACAGCCTGAGAGCCGAGGACACGGCTGTATATTACTGTGCGAGAGATCAC
TATGGTTCGGGGGTGCACCACTATTTCTACTACGGTCTGGACGTCTGGGG
CCAAGGGACCACGGTCACCGTCTCCTCAGCCTCCACCAAGGGCCCATCGG
TCTTCCCGCTAGCGCCCTGCTCCAGGAGCACCTCCGAGAGCACAGCCGCC
CTGGGCTGCCTGGTCAAGGACTACTTCCCCGAACCGGTGACGGTGTCGTG
GAACTCAGGCGCCCTGACCAGCGGCGTGCACACCTTCCCGGCTGTCCTAC
AGTCCTCAGGACTCTACTCCCTCAGCAGCGTGGTGACCGTGCCCTCCAGC
AGCTTGGGCACGAAGACCTACACCTGCAACGTAGATCACAAGCCCAGCAA
CACCAAGGTGGACAAGAGAGTTGAGTCCAAATATGGTCCCCCATGCCCAC
CCTGCCCAGCACCTGAGGCCGCCGGGGGACCATCAGTCTTCCTGTTCCCC
CCAAAACCCAAGGACACTCTCATGATCTCCCGGACCCCTGAGGTCACGTG
CGTGGTGGTGGACGTGAGCCAGGAAGACCCCGAGGTCCAGTTCAACTGGT
ACGTGGATGGCGTGGAGGTGCATAATGCCAAGACAAAGCCGCGGGAGGAG
CAGTTCAACAGCACGTACCGTGTGGTCAGCGTCCTCACCGTCCTGCACCA
GGACTGGCTGAACGGCAAGGAGTACAAGTGCAAGGTCTCCAACAAAGGCC
TCCCGTCCTCCATCGAGAAAACCATCTCCAAAGCCAAAGGGCAGCCCCGA
GAGCCACAGGTGTACACCCTGCCCCCATCCCAGGAGGAGATGACCAAGAA
CCAGGTCAGCCTGACCTGCCTGGTCAAAGGCTTCTACCCCAGCGACATCG
CCGTGGAGTGGGAAAGCAATGGGCAGCCGGAGAACAACTACAAGACCACG
CCTCCCGTGCTGGACTCCGACGGCTCCTTCTTCCTCTACAGCAGGCTAAC
CGTGGACAAGAGCAGGTGGCAGGAGGGGAATGTCTTCTCATGCTCCGTGA
TGCATGAGGCTCTGCACAACCACTACACACAGAAGAGCCTCTCCCTGTCT
CTGGGT SEQ ID NO: 15
(LC DNA- Antibody 1 and 2)
GAAATTGTGTTGACGCAGTCTCCAGGCACCCTGTCTTTGTCTCCAGGGGA
AAGAGCCACCCTCTCCTGCAGGGCCAGTCAGAGTGTTAGCAGCAGCTACT
TAGCCTGGTACCAGCAGAAACCTGGCCAGGCTCCCAGGCTCCTCATCTAT
GGTGCATCCAGCAGGGCCACTGGCATCCCAGACAGGTTCAGTGGCAGTGG
GTCTGGGACAGACTTCACTCTCACCATCAGCAGACTGGAGCCTGAAGATT
TTGCAGTGTATTACTGTCAGCAGTATGGTAGCTCACCGCTCACTTTCGGC -continued
GGAGGGACCAAGGTGGAGATCAAACGAACTGTGGCTGCACCATCTGTCTT
CATCTTCCCGCCATCTGATGAGCAGTTGAAATCTGGAACTGCCTCTGTTG
TGTGCCTGCTGAATAACTTCTATCCCAGAGAGGCCAAAGTACAGTGGAAG
GTGGATAACGCCCTCCAATCGGGTAACTCCCAGGAGAGTGTCACAGAGCA
GGACAGCAAGGACAGCACCTACAGCCTCAGCAGCACCCTGACGCTGAGCA
AAGCAGACTACGAGAAACACAAAGTCTACGCCTGCGAAGTCACCCATCAG
GGCCTGAGCTCGCCCGTCACAAAGAGCTTCAACAGGGGAGAGTGTTAG SEQ ID NO: 16
(HC - Antibody 3)
QVQLKESGPGLVRPSETLSLTCTVSGFSLSDYSLSWVRRPSGKGPEWLGR
LWFDGDTTYNSAFKSRLTISRDTSKDQVFLKMNSLQTDDTGTYYCTRDDR
DFDYWGQGVMVTVSSAETTAPSVYPLAPGTALKSNSMVTLGCLVKGYFPE
PVTVTWNSGALSSGVHTFPAVLQSGLYTLTSSVTVPSSTWPSQTVTCNVA
HPASSTKVDKKIVPRNCGGDCKPCICTGSEVSSVFIFPPKPKDVLTITLT
PKVTCVVVDISQDDPEVHFSWFVDDVEVHTAQTRPPEEQFNSTFRSVSEL
PILHQDWLNGRTFRCKVTSAAFPSPIEKTISKPEGRTQVPHVYTMSPTKE
EMTQNEVSITCMVKGFYPPDIYVEWQMNGQPQENYKNTPPTMDTDGSYFL
YSKLNVKKEKWQQGNTFTCSVLHEGLHNHHTEKSLSHSPGK SEQ ID NO: 17
(LC - Antibody 3)
DIVMTQTPVSMSVSLGGQVSISCRSSQSLVNNNGNTYLSWYIQKPSQSPQ
LLIYKVSNRVSGISDRFSGSGSGTDFTLKINKIEPDDLGVYYCGQNTQYP
LTFGSGTKLEIKRADAAPTVSIFPPSTEQLATGGASVVCLMNNFYPRDIS
VKWKIDGTERRDGVLDSVTDQDSKDSTYSMSSTLSLTKADYESHNLYTCE
VVHKTSSSPVVKSFNRNEC SEQ ID NO: 18
(HC - Antibody 4)
QVQLKESGPGLVRPSETLSLTCTVSGFSLSDYSLSWVRRPSGKGPEWLGR
LWFDGDTTYNSAFKSRLTISRDTSKDQVFLKMNSLQTDDTGTYYCTRDDR
DFDYWGQGVMVTVSSAKTTPPSVYPLAPGSAAQTNSMVTLGCLVKGYFPE
PVTVTWNSGSLSSGVHTFPAVLQSDLYTLSSSVTVPSSTWPSETVTCNVA
HPASSTKVDKKIVPRDCGCKPCICTVPEVSSVFIFPPKPKDVLTITLTPK
VTCVVVDISKDDPEVQFSWFVDDVEVHTAQTQPREEQFNSTFRSVSELPI
MHQDWLNGKEFKCRVNSAAFPAPIEKTISKTKGRPKAPQVYTIPPPKEQM
AKDKVSLTCMITDFFPEDITVEWQWNGQPAENYKNTQPIMDTDGSYFVYS
KLNVQKSNWEAGNTFTCSVLHEGLHNHHTEKSLSHSPG SEQ ID NO: 19
(LC - Antibody 4)
DIVMTQTPVSMSVSLGGQVSISCRSSQSLVNNNGNTYLSWYIQKPSQSPQ
LLIYKVSNRVSGISDRFSGSGSGTDFTLKINKIEPDDLGVYYCGQNTQYP
LTFGSGTKLEIKRADAAPTVSIFPPSSEQLTSGGASVVCFLNNFYPKDIN
VKWKIDGSERQNGVLNSWTDQDSKDSTYSMSSTLTLTKDEYERHNSYTCE
ATHKTSTSPIVKSFNRNEC

We claim:

1. A method of treating diabetic nephropathy in a patient, comprising administering to a patient in need thereof, an effective amount of a VEGFR1 antibody, wherein the VEGFR1 antibody is an antibody comprising a light chain variable region (LCVR) and a heavy chain variable region (HCVR), wherein the LCVR comprises the complementarity determining regions (CDRs) LCDR1, LCDR2, and LCDR3, and the HCVR comprises the CDRs HCDR1, HCDR2, and HCDR3, wherein the LCDR1 is the polypeptide consisting of the amino acid sequence of RASQSVSSSYLA (SEQ ID NO: 8), the LCDR2 is the polypeptide consisting of the amino acid sequence of GASSRAT (SEQ ID NO: 9), the LCDR3 is the polypeptide consisting of the amino acid sequence of QQYGSSPLT (SEQ ID NO: 10), the HCDR1 is the polypeptide consisting of the amino acid sequence of GFAFSSYGMH (SEQ ID NO: 2), the HCDR2 is the polypeptide consisting of the amino acid sequence of VIWYDGSNKYYADSVRG (SEQ ID NO: 3), and the HCDR3 is the polypeptide consisting of the amino acid sequence of DHYGSGVHHYFYYGLDV (SEQ ID NO: 4).

2. The method according to claim 1, wherein the patient is at stage 3 or stage 4 of diabetic nephropathy.

3. A method of decreasing proteinuria in a patient having diabetic nephropathy, comprising administering to a patient in need thereof, an effective amount of a VEGFR1 antibody, wherein the VEGFR1 antibody is an antibody comprising a light chain variable region (LCVR) and a heavy chain variable region (HCVR), wherein the LCVR comprises the complementarity determining regions (CDRs) LCDR1, LCDR2, and LCDR3, and the HCVR comprises the CDRs HCDR1, HCDR2, and HCDR3, wherein the LCDR1 is the polypeptide consisting of the amino acid sequence of RASQSVSSSYLA (SEQ ID NO: 8), the LCDR2 is the polypeptide consisting of the amino acid sequence of GASSRAT (SEQ ID NO: 9), the LCDR3 is the polypeptide consisting of the amino acid sequence of QQYGSSPLT (SEQ ID NO: 10), the HCDR1 is the polypeptide consisting of the amino acid sequence of GFAFSSYGMH (SEQ ID NO: 2), the HCDR2 is the polypeptide consisting of the amino acid sequence of VIWYDGSNKYYADSVRG (SEQ ID NO: 3), and the HCDR3 is the polypeptide consisting of the amino acid sequence of DHYGSGVHHYFYYGLDV (SEQ ID NO: 4).

4. A method of decreasing albuminuria in a patient having diabetic nephropathy, comprising administering to a patient in need thereof, an effective amount of a VEGFR1 antibody, wherein the VEGFR1 antibody is an antibody comprising a light chain variable region (LCVR) and a heavy chain variable region (HCVR), wherein the LCVR comprises the complementarity determining regions (CDRs) LCDR1, LCDR2, and LCDR3, and the HCVR comprises the CDRs HCDR1, HCDR2, and HCDR3, wherein the LCDR1 is the polypeptide consisting of the amino acid sequence of RASQSVSSSYLA (SEQ ID NO: 8), the LCDR2 is the polypeptide consisting of the amino acid sequence of GASSRAT (SEQ ID NO: 9), the LCDR3 is the polypeptide consisting of the amino acid sequence of QQYGSSPLT (SEQ ID NO: 10), the HCDR1 is the polypeptide consisting of the amino acid sequence of GFAFSSYGMH (SEQ ID NO: 2), the HCDR2 is the polypeptide consisting of the amino acid sequence of VIWYDGSNKYYADSVRG (SEQ ID NO: 3), and the HCDR3 is the polypeptide consisting of the amino acid sequence of DHYGSGVHHYFYYGLDV (SEQ ID NO: 4).

5. The method according to claim 1 wherein the VEGFR1 antibody comprises a LCVR that is the polypeptide consisting of the amino acid sequence of SEQ ID NO: 11, and a HCVR that is the polypeptide consisting of the amino acid sequence of SEQ ID NO: 5.

6. The method according to claim 2 wherein the VEGFR1 antibody comprises a LCVR that is the polypeptide consisting of the amino acid sequence of SEQ ID NO: 11, and a HCVR that is the polypeptide consisting of the amino acid sequence of SEQ ID NO: 5.

7. The method according to claim 3 wherein the VEGFR1 antibody comprises a LCVR that is the polypeptide consisting of the amino acid sequence of SEQ ID NO: 11, and a HCVR that is the polypeptide consisting of the amino acid sequence of SEQ ID NO: 5.

8. The method according to claim 4 wherein the VEGFR1 antibody comprises a LCVR that is the polypeptide consisting of the amino acid sequence of SEQ ID NO: 11, and a HCVR that is the polypeptide consisting of the amino acid sequence of SEQ ID NO: 5.

* * * * *